(12) United States Patent
Inoue et al.

(10) Patent No.: US 9,561,235 B2
(45) Date of Patent: Feb. 7, 2017

(54) PREVENTIVE OR THERAPEUTIC AGENT FOR PAIN ASSOCIATED WITH HERPES ZOSTER IN ACUTE PHASE

(71) Applicants: KYUSHU UNIVERSITY, Fukuoka-shi, Fukuoka (JP); NIPPON CHEMIPHAR CO., LTD., Chiyoda-ku, Tokyo (JP)

(72) Inventors: Kazuhide Inoue, Fukuoka (JP); Makoto Tsuda, Fukuoka (JP); Yuta Matsumura, Fukuoka (JP)

(73) Assignees: Kyushu University, Fukuoka (JP); Nippon Chemiphar Co., LTD., Tokyo (JP)

(*) Notice: Subject to any disclaimer, the term of this patent is extended or adjusted under 35 U.S.C. 154(b) by 0 days.

(21) Appl. No.: 14/808,609

(22) Filed: Jul. 24, 2015

(65) Prior Publication Data
US 2015/0328231 A1 Nov. 19, 2015

Related U.S. Application Data

(63) Continuation of application No. 13/882,205, filed as application No. PCT/JP2011/075244 on Nov. 2, 2011, now Pat. No. 9,115,123.

(30) Foreign Application Priority Data

Nov. 5, 2010 (JP) .................... 2010-248173

(51) Int. Cl.
A61K 31/5513 (2006.01)
C07D 243/38 (2006.01)
A61K 31/135 (2006.01)
A61K 31/138 (2006.01)
A61K 31/15 (2006.01)
A61K 31/335 (2006.01)
A61K 31/343 (2006.01)
A61K 31/451 (2006.01)
A61K 31/4525 (2006.01)
A61K 31/495 (2006.01)
A61K 31/55 (2006.01)
A61K 31/551 (2006.01)
C07D 313/12 (2006.01)
C07D 223/28 (2006.01)
C07D 405/12 (2006.01)
C07D 413/10 (2006.01)
(Continued)

(52) U.S. Cl.
CPC ......... *A61K 31/5513* (2013.01); *A61K 31/135* (2013.01); *A61K 31/138* (2013.01); *A61K 31/15* (2013.01); *A61K 31/335* (2013.01); *A61K 31/343* (2013.01); *A61K 31/451* (2013.01); *A61K 31/4525* (2013.01); *A61K 31/495* (2013.01); *A61K 31/55* (2013.01); *A61K 31/551* (2013.01); *C07D 223/28* (2013.01); *C07D 307/87* (2013.01); *C07D 313/12* (2013.01); *C07D 405/12* (2013.01); *C07D 413/10* (2013.01); *C07D 413/12* (2013.01)

(58) Field of Classification Search
CPC .................... A61K 31/5513; C07D 243/38
See application file for complete search history.

(56) References Cited

U.S. PATENT DOCUMENTS

| | | | |
|---|---|---|---|
| 8,470,814 | B2 | 6/2013 | Sakuma et al. |
| 2002/0077342 | A1 | 6/2002 | Blakemore et al. |
| 2003/0203945 | A1 | 10/2003 | Blakemore et al. |

(Continued)

FOREIGN PATENT DOCUMENTS

| | | |
|---|---|---|
| JP | 2009-062278 | 3/2009 |
| JP | 2012-087053 | 5/2012 |

(Continued)

OTHER PUBLICATIONS

Extended European Search Report, PCT/JP2011/075244 dated Mar. 4, 2014.
(Continued)

*Primary Examiner* — Erich A Leeser
(74) *Attorney, Agent, or Firm* — Nixon Peabody LLP; Jeffrey L. Costellia

(57) ABSTRACT

A $P2X_4$ receptor antagonist such as paroxetine, a diazepinedione derivative having the following formula (IX) is used as an agent for preventing or treating zoster-associated pain in acute phase:

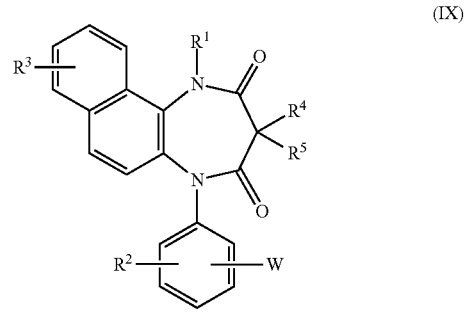

(IX)

wherein $R^1$ is hydrogen, a $C_{1-8}$ alkyl group, or the like;
each of $R^2$ and $R^3$ is hydrogen, a $C_{1-8}$ alkyl group, or the like;
each of $R^4$ and $R^5$ is hydrogen or the like; and
W is a five-membered or six-membered heterocyclic ring optionally having one or more substituents and comprising one to four nitrogen atoms as the members of the ring.

5 Claims, 3 Drawing Sheets

(51) Int. Cl.
*C07D 307/87* (2006.01)
*C07D 413/12* (2006.01)

(56) References Cited

U.S. PATENT DOCUMENTS

| | | |
|---|---|---|
| 2010/0256123 A1 | 10/2010 | Sakuma et al. |
| 2011/0092703 A1 | 4/2011 | Sakuma et al. |
| 2011/0319610 A1 | 12/2011 | Sakuma et al. |
| 2012/0116073 A1 | 5/2012 | Sakuma et al. |
| 2012/0172550 A1 | 7/2012 | Ferrer et al. |
| 2013/0172550 A1 | 7/2013 | Sakuma et al. |
| 2014/0163013 A1 | 6/2014 | Imai et al. |

FOREIGN PATENT DOCUMENTS

| | | | | |
|---|---|---|---|---|
| WO | WO2008/020651 | | 2/2008 | |
| WO | WO2010/093061 | | 8/2010 | |
| WO | WO 2010093061 | * | 8/2010 | ........... C07D 403/10 |

OTHER PUBLICATIONS

International Perliminary Report on Patentability dated May 8, 2013 and Written Opinion dated Feb. 7, 2012 in Application No. PCT/JP2011/075244.
J. Fashner, MD, et al., "Herpes Zoster and Postherpetic Neuralgia: Prevention and Management", American Academy of Family Physicians, Jun. 15, 2011, vol. 83, No. 12, pp. 1432-1437.
Y. Kurashi, "Mechanisms of Herpetic Pain and Postherpetic Neuralgia", Graduate School of Medicine and Pharmaceutical Sciences, University of Toyama, Neuro, 2010.
B. Yawn, et al., "Herpes Zoster Recurrences More Frequent Than Previously Reported", Mayo Clin. Proc., Feb. 2011, vol. 86(2), pp. 88-93.
J. Coulehan, "Shingles Does It", *Health Affairs*, vol. 28, No. 5, (2009): pp. 1509-1514.
R. Johnson, "Herpes-Zoster—Predicting and Minimizing the Impact of Post-Herpetic Neuralgia", *Journal of Antimicrobial Chemotherapy*, (2001), vol. 47, *Topic T1*, pp. 1-8.
M. Wood, "Understanding Pain in Herpes Zoster: An Essential for Optimizing Treatment", The Journal of Infectious Diseases, 2002, 186 (Suppl I), pp. S78-S82.
M. Tsuda et al., "Behavioral Phenotypes of Mice Lacking Purinergic $P2X_4$ Receptors in Acute and Chronic Pain Assays", Molecular Pain, 2009, vol. 5:28, pp. 1-7.
M. Tsuda et al., "$P2X_4$ Receptors Induced in Spinal Microglia Gate Tactile Allodynia After Nerve Injury", Nature, Aug. 14, 2003, vol. 434, pp. 778-783.
L. Leventhal et al., "Differential and Synergistic Effects of Selective Norepinephrine and Serotonin Reuptake Inhibitors in Rodent Models of Pain", The Journal of Pharmacology and Experimental Therapeutics, 2007, vol. 320, No. 3, pp. 1178-1185.
L. Bardin et al., "Profound, Non-Opioid Analgesia Produced by the High-Efficacy $5-HY_{1A}$ Agonist F 13640 in the Formalin Model of Tonic Nociceptive Pain", Pharmacology, 2003, vol. 67, pp. 182-194.
K. Nagata et al., "Antidepressants Inhibit $P2X_4$ Receptor Function: A Possible Involvement in Neuropathic Pain Relief", *Molecular Pain*, 2009, vol. 5, No. 20, pp. 1-12.
Ohno, "Role of Extracellular Nucleotides and Their Receptors in Chronic Pain", Journal of Biochemistry, 2009, vol. 81, No. 10, pp. 884-890.
Hernandez-Olmos, et al., "N-Substituted Phenoxazine and Acridone Derivatives: Structure-Activity Relationships of Potent P2X4 Receptor Antagonists", J. Med. Chem. 2012, 55, 9576-9588.
Schulzeck Sabine et al. (written in German); Herpetic Neuralgia, Pain Therapy of the Acute Phase and the Postherpetic Neuralgia; Dated 2009 (8 pages).
Schulzeck Sabine et al. (English Translation); Herpetic Neuralgia, Pain Therapy of the Acute Phase and the Postherpetic Neuralgi; Dated 2009 (16 pages).
Gonzalez Martinez F. (written in Spanish); Letters to the Director, Utilization of Corticoids in the Treatment of Neuropathic Pain of Acute Herpes Zoster; Dated Apr. 20, 1999; (2 Pages).
Gonzalez Martinez F. (English Translation); Letters to the Director, Utilization of Corticoids in the Treatment of Neuropathic Pain of Acute Herpes Zoster; Dated Apr. 20, 1999; (2 Pages).

* cited by examiner

Double staining images of P2X$_4$ and microglia

PREVENTIVE OR THERAPEUTIC AGENT FOR PAIN ASSOCIATED WITH HERPES ZOSTER IN ACUTE PHASE

FIELD OF THE INVENTION

The present invention relates to an agent for preventing or treating zoster-associated pain in acute phase.

BACKGROUND OF THE INVENTION

Herpes zoster is a viral disease caused by a varicella zoster virus (VZV). Initial infection of VZV is usually in childhood to cause varicella. The infected host may acquire humoral and cellular immunities against VZV to cease proliferation of virus. At the same time, virus may partly be incorporated into the peripheral end of sensory nerve fibers distributed in the skin, ascend the sensory nerve fiber along a retrograde axonal flow, and cause latent infection in ganglion. When the specific cellular immunity against VZV is lowed in the host, virus is reactivated to develop the syndrome of the herpes zoster. The reactivated virus descends the sensory nerve fiber along an antegrade axonal flow to reach the skin and cause zonary exanthema. The exanthema is naturally healed generally within about three weeks.

The zoster-associated pain is generally classified into an acute phase pain and a chronic phase pain. The chronic phase pain is a general problem, which continues over a long term after healing the exanthema. The chronic phase pain is called postherpetic neuralgia, which is considered as neuropathic pain caused by neural degeneration in central and peripheral nervous systems (Non-patent documents 1, 2, and 3). Tricyclic antidepressant, opioid, antiepileptic drugs or the like are used for the present to treat postherpetic neuralgia, and their treatment effects are reported.

On the other hand, the acute phase pain is prodrome or pain in an acute phase, which causes neuralgia-like pain several days before development of exanthema. It includes neuritis pain caused by proliferated virus and inflammatory pain within the area of exanthema. The area of exanthema can be the center of algesthesia, and pain runs along the nerve. The strength of the pain widely ranges from lightly stimulated symptom to heavy pain losing sleep at night. A HSV-1 infected rat has been used as a herpes zoster model. It has been confirmed that the rat can be spontaneously excited without inflammatory syndrome in the spinal posterior root ganglion. It is suggested that acute phase pain may be expressed with spontaneous hypersthenia of the primary neuron cell body (Non-patent document 4).

The acute phase of herpes zoster is treated for the present by using a combination of antiviral agent such as Valaciclovir, Aciclovir, Famciclovir or the like with an analgesic such as NSAIDs. The NSAIDs has an effect on inflammatory pain, but no effect on neuritis-like pain. Further, whole body administration of opioid is sometimes used. It has been known that the above-mentioned pharmacotherapy can have an accelerating effect of healing exanthema, and show a partial effect on acute phase pain, but it cannot suppress the pain completely. Therefore, nerve block treatments, such as epidural block, stellate block, peripheral nerve block has been used in the case that the exanthema and pain are serious (Non-patent document 5). For the reasons mentioned above, it has been desired to develop a method of treating acute phase of herpes zoster pain in view of QOL of the herpes zoster patients.

The present inventors have found that paroxetine, a diazepinedione derivative or the like having a P2X$_4$ receptor antagonism can be used as an agent for preventing or treating neuropathic pain, and filed patent applications (Patent documents 1 and 2).

The patent documents, however, do not clearly describe that the above-mentioned compounds are available as an agent for preventing or treating zoster-associated pain in acute phase.

PRIOR ART DOCUMENTS

Patent Documents

Patent document 1: WO 2008/020651
Patent document 2: WO 2010/093061

Non-Patent Documents

Non-patent document 1: Oaklander A L., Pain, 2001, 92:139-145
Non-patent document 2: Watson C P, et al., Pain, 1991, 44:105-117
Non-patent document 3: Rowbotham M C, et al., Neurobiol Dis, 1996, 3:205-214
Non-patent document 4: Fleetwood-Walker S M, et al., J Gen Virol., 1999, 80:2433-2436
Non-patent document 5: Kazushige Kawamura et al., the Progress of Medicine, 2007, Vol. 223, No 9:40-42

SUMMARY OF THE INVENTION

Problems to be Solved by the Invention

It is the object of the invention to provide an agent for preventing or treating zoster-associated pain in acute phase.

Means for Solving the Problems

The present inventors have found that P2X$_4$ receptor antagonist such as paroxetine, a diazepinedione derivative or the like can be used as an agent for preventing or treating zoster-associated pain in acute phase, and completed the present invention.

The present invention relates to an agent for preventing or treating zoster-associated pain in acute phase containing P2X$_4$ receptor antagonist as an active ingredient.

The invention also relates to an agent for preventing or treating zoster-associated pain in acute phase containing a compound having the following formula (I) or a pharmacologically acceptable salt thereof as an active ingredient:

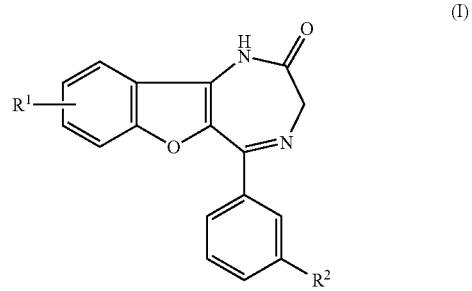

(I)

wherein R$^1$ is a halogen atom; and
R$^2$ is hydrogen, a halogen atom, nitro, cyano, —C(O)—OR$^3$, —C(O)—NR$^4$R$^5$, —SO$_2$—OR$^3$, —SO$_2$—NR$^4$R$^5$, wherein each of R$^3$, R$^4$, and R$^5$ is hydrogen or a C$_{1-6}$ alkyl group; or in the alternative
R$^1$ is hydrogen; and $R^2$ is a halogen atom, nitro, cyano, —C(O)—OR$^3$, —C(O)—NR$^4$R$^5$, —SO$_2$—OR$^3$, —SO$_2$—NR$^4$R$^5$, wherein each of R$^3$, R$^4$, and R$^5$ is hydrogen or a C$_{1-6}$ alkyl group.

The invention further relates to an agent for preventing or treating zoster-associated pain in acute phase containing a compound having the following formula (Ia) or a pharmacologically acceptable salt thereof as an active ingredient:

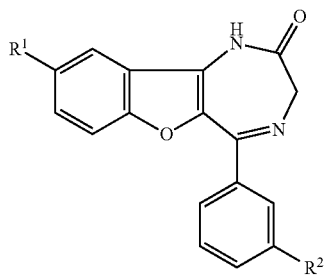

(Ia)

wherein R$^1$ is chloro or bromo; and

R$^2$ is hydrogen, chloro, bromo, nitro, or cyano; or in the alternative

R$^1$ is hydrogen; and

R$^2$ is chloro, bromo, nitro, or cyano.

The invention further relates to an agent for preventing or treating zoster-associated pain in acute phase containing a compound having the following formula (II) or a pharmacologically acceptable salt thereof as an active ingredient:

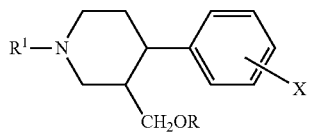

(II)

wherein R is a C$_{1-4}$ alkyl group, a C$_{2-4}$ alkynyl group, phenyl optionally having one or more substituents selected from the group consisting of a lower alkyl group, an alkylthio group, an alkoxy group, a halogen atom, nitro, an acylamino group, methylsulfonyl, and methylenedioxy, or tetrahydronaphthyl;

R$^1$ is hydrogen; and

X is hydrogen, a C$_{1-4}$ alkyl group, a trifluoroalkyl group, hydroxyl, a halogen atom, methylthio, or an arylalkoxy group.

The invention further relates to an agent for preventing or treating zoster-associated pain in acute phase containing a selective serotonin reuptake inhibitor as an active ingredient.

The invention further relates to an agent for preventing or treating zoster-associated pain in acute phase containing an agent selected from the group consisting of imipramine, nortriptyline, amitriptyline, desipramine, doxepin, fluoxetine, fluvoxamine, citalopram, and a pharmacologically acceptable salt thereof as an active ingredient.

The invention further relates to an agent for preventing or treating zoster-associated pain in acute phase containing a compound having the following formula (III) or a pharmacologically acceptable salt thereof as an active ingredient:

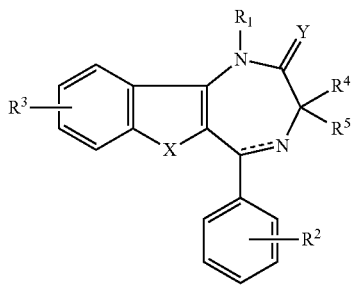

(III)

wherein X is S or CH$_2$;

Y is O, S, or NH;

R$^1$ is hydrogen, a C$_{1-8}$ alkyl group, a C$_{1-8}$ alkyl group having one or more halogen atoms, an aralkyl group comprising a C$_{1-6}$ alkyl moiety and a C$_{6-10}$ aryl moiety, a C$_{2-8}$ alkenyl group, carboxymethyl, or an alkoxycarbonylmethyl group comprising a C$_{1-8}$ alkoxy moiety;

each of R$^2$ and R$^3$ independently is hydrogen, a C$_{1-8}$ alkyl group, a C$_{1-8}$ alkoxy group, a C$_{1-8}$ alkyl group having one or more halogen atoms, a C$_{1-8}$ alkoxy group having one or more halogen atoms, a halogen atom, amino, carboxyl, hydroxyl, nitro, cyano, a C$_{2-8}$ acyl group, a C$_{6-10}$ aryl group, or a five-membered or six-membered heterocyclic group;

each of R$^4$ and R$^5$ independently is hydrogen, a C$_{1-8}$ alkyl group, or a C$_{1-8}$ alkyl group having one or more halogen atoms; and the double line consisting of a broken line and a solid line is a single bond or a double bond.

The invention further relates to an agent for preventing or treating zoster-associated pain in acute phase containing a compound having the following formula (IV) or a pharmacologically acceptable salt thereof as an active ingredient:

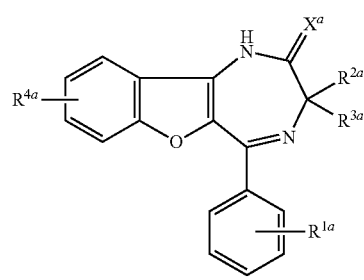

(IV)

wherein X$^a$ is O, S, or NH;

R$^{1a}$ is hydroxyl, tetrazolyl, N(R$^{5a}$)(R$^{6a}$), a C$_{2-8}$ alkenyl group, a C$_{2-8}$ alkynyl group, a C$_{1-8}$ alkyl group having one or more halogen atoms, a C$_{1-8}$ alkoxy group having one or more halogen atoms, or a C$_{6-10}$ aryl group, wherein R$^{5a}$ is hydrogen or a C$_{1-8}$ alkyl group, and R$^{6a}$ is hydrogen, a C$_{1-8}$ alkyl group, or a C$_{2-8}$ acyl group;

each of R$^{2a}$ and R$^{3a}$ independently is hydrogen, a C$_{1-8}$ alkyl group, or a C$_{1-8}$ alkyl group having one or more halogen atoms; and R$^{4a}$ is hydrogen, a C$_{1-8}$ alkyl group, a C$_{1-8}$ alkoxy group, a C$_{1-8}$ alkyl group having one or more halogen atoms, a halogen atom, hydroxyl, nitro, amino, carboxyl, tetrazolyl, cyano, a C$_{6-10}$ aryl group, or a five-membered or six-membered heterocyclic group.

The invention further relates to an agent for preventing or treating zoster-associated pain in acute phase containing a compound having the following formula (IVa) or a pharmacologically acceptable salt thereof as an active ingredient:

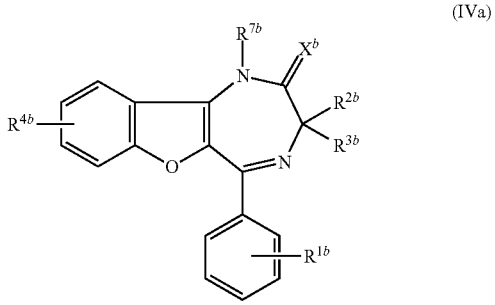

(IVa)

wherein $X^b$ is O, S, or NH;

$R^{1b}$ is a halogen atom, hydroxyl, tetrazolyl, $N(R^{5b})(R^{6b})$, a $C_{2-8}$ alkenyl group, a $C_{2-8}$ alkynyl group, a $C_{1-8}$ alkyl group having one or more halogen atoms, a $C_{1-8}$ alkoxy group having one or more halogen atoms, or a $C_{6-10}$ aryl group, wherein $R^{5b}$ is hydrogen or a $C_{1-8}$ alkyl group, and $R^{6b}$ is hydrogen, a $C_{1-8}$ alkyl group, or a $C_{2-8}$ acyl group;

each of $R^{2b}$ and $R^{3b}$ independently is hydrogen, a $C_{1-8}$ alkyl group, or a $C_{1-8}$ alkyl group having one or more halogen atoms;

$R^{4b}$ is hydrogen, a $C_{1-8}$ alkyl group, an alkoxy group, a $C_{1-8}$ alkyl group having one or more halogen atoms, a halogen atom, hydroxyl, nitro, amino, carboxyl, tetrazolyl, cyano, a $C_{6-10}$ aryl group, or a five-membered or six-membered heterocyclic group; and $R^{7b}$ is a $C_{1-8}$ alkyl group.

The invention further relates to an agent for preventing or treating zoster-associated pain in acute phase containing a compound having the following formula (IVb) or a pharmacologically acceptable salt thereof as an active ingredient:

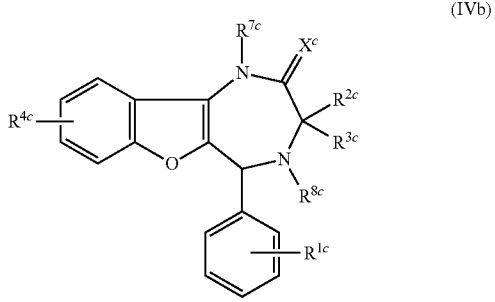

(IVb)

wherein $X^c$ is O, S, or NH;

$R^{1c}$ is hydrogen, a halogen atom, a $C_{1-8}$ alkyl group, a $C_{1-8}$ alkoxy group, hydroxyl, tetrazolyl, $N(R^{5c})(R^{6c})$, a $C_{2-8}$ alkenyl group, a $C_{2-8}$ alkynyl group, a $C_{1-8}$ alkyl group having one or more halogen atoms, a $C_{1-8}$ alkoxy group having one or more halogen atoms, or a $C_{6-10}$ aryl group, wherein $R^{5c}$ is hydrogen or a $C_{1-8}$ alkyl group, and $R^{6c}$ is hydrogen, a $C_{1-8}$ alkyl group, or a $C_{2-8}$ acyl group;

each of $R^{2c}$ and $R^{3c}$ independently is hydrogen, a $C_{1-8}$ alkyl group, or a $C_{1-8}$ alkyl group having one or more halogen atoms;

$R^{4c}$ is hydrogen, a $C_{1-8}$ alkyl group, an alkoxy group, a $C_{1-8}$ alkyl group having one or more halogen atoms, a halogen atom, hydroxyl, nitro, amino, carboxyl, tetrazolyl, cyano, a $C_{6-10}$ aryl group, or a five-membered or six-membered heterocyclic group;

$R^{7c}$ is hydrogen or a $C_{1-8}$ alkyl group; and $R^{8c}$ is hydrogen, a $C_{1-8}$ alkyl group, or a $C_{2-8}$ acyl group.

The invention further relates to an agent for preventing or treating zoster-associated pain in acute phase containing a compound having the following formula (V) or a pharmacologically acceptable salt thereof as an active ingredient:

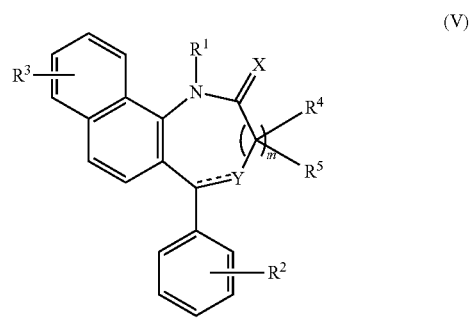

(V)

wherein X is O, S, or NH;

Y is N or $NR^6$, wherein $R^6$ is hydrogen or a $C_{1-8}$ alkyl group;

$R^1$ is hydrogen, a $C_{1-8}$ alkyl group, a $C_{2-8}$ alkenyl group, a $C_{1-8}$ alkyl group having one to three halogen atoms, or an alkyl group having phenyl;

$R^2$ is a $C_{1-8}$ alkyl group, a $C_{1-8}$ alkoxy group, a $C_{1-8}$ alkyl group having one to three halogen atoms, hydroxyl, nitro, amino, carboxyl, tetrazolyl, or cyano;

$R^3$ is hydrogen, a $C_{1-8}$ alkyl group, a $C_{1-8}$ alkoxy group, a $C_{1-8}$ alkyl group having one to three halogen atoms, a halogen atom, hydroxyl, nitro, amino, carboxyl, tetrazolyl, or cyano;

each of $R^4$ and $R^5$ independently is hydrogen, a $C_{1-8}$ alkyl group, or a $C_{1-8}$ alkyl group having one to three halogen atoms;

m is 1 or 2;

when Y is N, the double line consisting of a solid line and a broken line is a double bond; and when Y is $NR^6$, the double line consisting of a solid line and a broken line is a single bond.

The invention further relates to An agent for preventing or treating zoster-associated pain in acute phase containing a compound having the following formula (Va) or a pharmacologically acceptable salt thereof as an active ingredient:

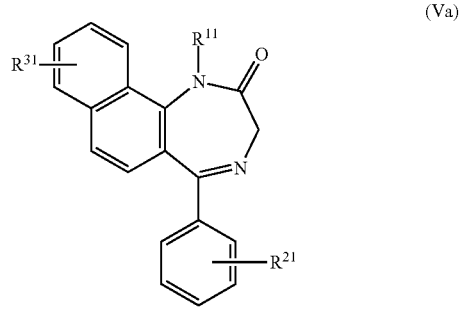

(Va)

wherein $R^{11}$ is hydrogen or a $C_{1-8}$ alkyl group;

$R^{21}$ is a $C_{1-8}$ alkyl group, a $C_{1-8}$ alkoxy group, a $C_{1-8}$ alkyl group having one to three halogen atoms, or hydroxyl; and $R^{31}$ is hydrogen or a halogen atom.

The invention further relates to an agent for preventing or treating zoster-associated pain in acute phase containing a compound having the following formula (VI) or a pharmacologically acceptable salt thereof as an active ingredient:

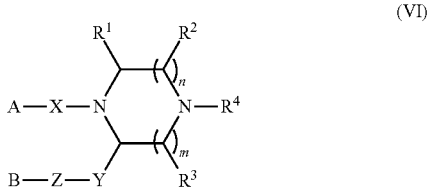

(VI)

wherein A is an aryl group optionally having one or more substituents or a heterocyclic group optionally having one or more substituents;

B is an aryl group optionally having one or more substituents or a heterocyclic group optionally having one or more substituents;

X is a $C_{1-5}$ alkylene group or a bond;

Y is a $C_{1-5}$ alkylene optionally comprising a double bond;

Z is O, S, N($R^5$), or a bond, wherein $R^5$ is hydrogen or a $C_{1-8}$ alkyl group;

each of $R^1$, $R^2$, and $R^3$ independently is hydrogen, a $C_{1-8}$ alkyl group, or a $C_{1-8}$ alkyl group having one to three halogen atoms;

$R^4$ is hydrogen, a $C_{1-8}$ alkyl group, a $C_{1-8}$ alkyl group having one to three halogen atoms, a three-membered to seven-membered cycloalkyl group, or a $C_{1-8}$ alkyl group having a three-membered to seven-membered cycloalkyl group; and each of n and m independently is 1 or 2;

provided that the substituent of the aryl group represented by A is not an alkyl group when X is a bond.

The invention further relates to an agent for preventing or treating zoster-associated pain in acute phase containing a compound having the following formula (VIa) or a pharmacologically acceptable salt thereof as an active ingredient:

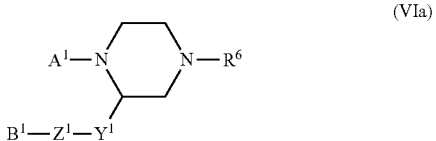

(VIa)

wherein $A^1$ is phenyl or thienyl, each of which optionally has one to three substituents selected from the group consisting of a halogen atom, a $C_{1-8}$ alkyl group having one to three halogen atoms, nitro, cyano, hydroxyl, amino, a $C_{1-8}$ alkylamino group, a $C_{2-16}$ dialkylamino group, a $C_{2-8}$ acylamino group, a $C_{1-8}$ alkoxy group, a $C_{1-8}$ alkoxy group having one to three halogen atoms, an aryl group, and a heterocyclic group;

$B^1$ is an aryl group optionally having one or more substituents or a heterocyclic group optionally having one or more substituents;

$Y^1$ is a $C_{1-5}$ alkylene chain optionally comprising a double bond;

$Z^1$ is O, S, N($R^7$), or a bond, wherein $R^7$ is hydrogen or a $C_{1-8}$ alkyl group; and $R^6$ is hydrogen, a $C_{1-8}$ alkyl group, a $C_{1-8}$ alkyl group having one to three halogen atoms, or a three-membered to seven-membered cycloalkyl group.

The invention further relates to an agent for preventing or treating zoster-associated pain in acute phase containing a compound having the following formula (VIb) or a pharmacologically acceptable salt thereof as an active ingredient:

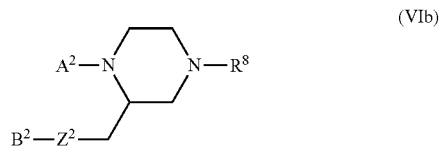

(VIb)

wherein $A^2$ is phenyl or thienyl, each of which optionally has one to three substituents selected from the group consisting of a halogen atom, a $C_{1-8}$ alkyl group having one to three halogen atoms, nitro, cyano, acetylamino, a $C_{1-8}$ alkoxy group, a $C_{1-8}$ alkoxy group having one to three halogen atoms, an aryl group, and a heterocyclic group;

$B^2$ is phenyl, naphthyl, benzofuranyl, 1,3-benzo[d]dioxolyl, quinolyl, indolyl, benzothienyl, thienyl, or pyridyl, each of which optionally has one to three substituents selected from the group consisting of a halogen atom, a $C_{1-8}$ alkyl group, a $C_{1-8}$ alkyl group having one to three halogen atoms, nitro, cyano, hydroxyl, amino, a $C_{2-8}$ acylamino group, a $C_{1-8}$ alkoxy group, a $C_{1-8}$ alkoxy group having one to three halogen atoms, a $C_{6-12}$ aryloxy group, sulfamoyl, a $C_{1-8}$ alkylsulfamoyl group, and a $C_{2-16}$ dialkylsulfamoyl group;

$Z^2$ is O, S, or NH; and $R^8$ is hydrogen or a $C_{1-8}$ alkyl group.

The invention further relates to an agent for preventing or treating zoster-associated pain in acute phase containing a compound having the following formula (VII) or a pharmacologically acceptable salt thereof as an active ingredient:

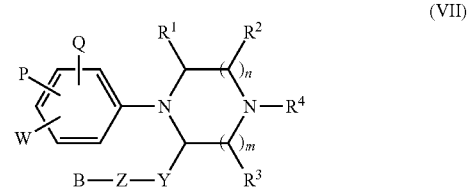

(VII)

wherein B is an aryl group optionally having one or more substituents or a heterocyclic group optionally having one or more substituents;

Y is a $C_{1-5}$ alkylene optionally comprising a double bond;

Z is O, S, N($R^5$), or a bond, wherein $R^5$ is hydrogen or a $C_{1-8}$ alkyl group;

each of $R^1$, $R^2$, and $R^3$ independently is hydrogen, a $C_{1-8}$ alkyl group, or a $C_{1-8}$ alkyl group having one to three halogen atoms;

$R^4$ is hydrogen, a $C_{1-8}$ alkyl group, a $C_{1-8}$ alkyl group having one to three halogen atoms, a three-membered to seven-membered cycloalkyl group, or a $C_{1-8}$ alkyl group having a three-membered to seven-membered cycloalkyl group;

each of P and Q independently is hydrogen, a halogen atom, a $C_{1-8}$ alkyl group, a $C_{1-8}$ alkyl group having one to three halogen atoms, nitro, cyano, hydroxyl, amino, a $C_{1-8}$ alkylamino group, a $C_{2-16}$ dialkylamino group, a $C_{2-8}$ acylamino group, a $C_{1-8}$ alkoxy group, a $C_{1-8}$ alkoxy group having one to three halogen atoms, or a heterocyclic group;

W is a $C_{1-8}$ alkyl group or a three-membered to seven-membered cycloalkyl group; or P and W are combined to form propylene or tetramethylene when P and W are placed at 2- and 3-positions or 3- and 4-positions of phenyl; and each of n and m independently is 1 or 2.

The invention further relates to an agent for preventing or treating zoster-associated pain in acute phase containing a compound having the following formula (VIII) or a pharmacologically acceptable salt thereof as an active ingredient:

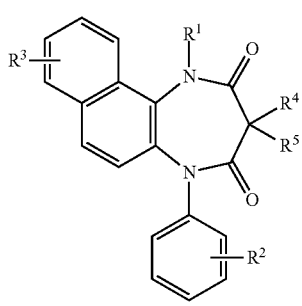

(VIII)

wherein $R^1$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

$R^2$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, carboxyl, a $C_{2-8}$ acyl group, or an alkoxycarbonyl group comprising a $C_{1-8}$ alkoxy moiety; and each of $R^4$ and $R^5$ independently is hydrogen, a $C_{1-8}$ alkyl group, or a $C_{1-8}$ alkyl group having one to three halogen atoms.

The invention further relates to an agent for preventing or treating zoster-associated pain in acute phase containing a compound having the following formula (IX) or a pharmacologically acceptable salt thereof as an active ingredient:

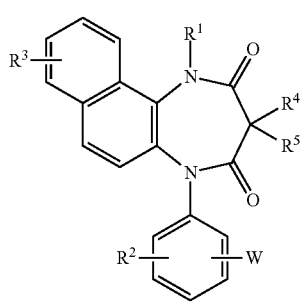

(IX)

wherein $R^1$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^2$ and $R^3$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

each of $R^4$ and $R^5$ independently is hydrogen, a $C_{1-8}$ alkyl group, a $C_{1-8}$ alkyl group having one to three halogen atoms, or a $C_{1-3}$ alkyl group having phenyl; and W is a five-membered or six-membered heterocyclic ring optionally having one or more substituents and comprising one to four nitrogen atoms as the members of the ring.

The invention further relates to an agent for preventing or treating zoster-associated pain in acute phase containing 5-[3-(5-thioxo-4H-[1,2,4]oxadiazol-3-yl)phenyl]-1H-naphtho[1,2-b][1,4]diazepine-2,4(3H,5H)-dione sodium salt as an active ingredient.

The invention further relates to an agent for preventing or treating zoster-associated pain in acute phase containing paroxetine or a pharmacologically acceptable salt thereof as an active ingredient.

The invention further relates to an agent for preventing or treating zoster-associated pain in acute phase containing a diazepine derivative having the following formula (X) or a pharmacologically acceptable salt thereof as an active ingredient:

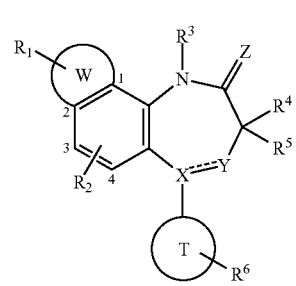

(X)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^4$ and $R^5$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^6$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered non-aromatic ring optionally comprising one or two heteroatoms selected from N, S, and O, and being condensed with the benzene ring at 1- and 2-positions of the benzene ring;

the ring shown below is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring;

Z is O or S;
when X is N, Y is C=O or C=S, and the double line consisting of a solid line and a broken line is a single bond; and
when X is C, Y is N, and the double line consisting of a solid line and a broken line is a double bond.

The invention further relates to an agent for preventing or treating zoster-associated pain in acute phase containing a diazepine derivative having the following formula (Xa) or a pharmacologically acceptable salt thereof as an active ingredient:

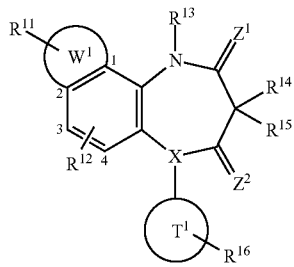

(Xa)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^{14}$ and $R^{15}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{16}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered non-aromatic ring optionally comprising one or two heteroatoms selected from N, S, and O, and being condensed with the benzene ring at 1- and 2-positions of the benzene ring;

the ring shown below is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring; and

each of $Z^1$ and $Z^2$ independently is O or S.

The invention further relates to an agent for preventing or treating zoster-associated pain in acute phase containing a diazepine derivative having the following formula (Xb) or a pharmacologically acceptable salt thereof as an active ingredient:

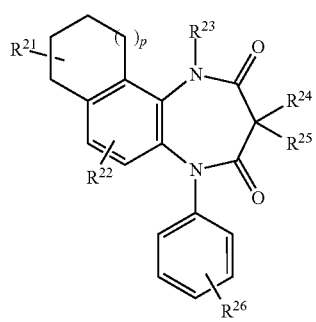

(Xb)

wherein each of $R^{21}$ and $R^{22}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{23}$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^{24}$ and $R^{25}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and p is 0 or 1.

The invention further relates to an agent for preventing or treating zoster-associated pain in acute phase containing a diazepine derivative having the following formula (XI) or a pharmacologically acceptable salt thereof as an active ingredient:

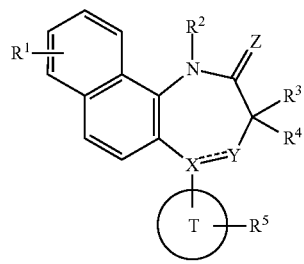

(XI)

wherein $R^1$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^2$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^3$ and $R^4$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^5$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

X is C or N;

the ring shown below is a heterocyclic ring selected from the group consisting of thiophene ring, pyridine ring, pyrimidine ring, quinoline ring, indole ring, indoline ring, benzimidazole ring, indazole ring, benzisoxazole ring, and benzotriazole ring, and the ring is combined with X at the carbon atom contained in the heterocyclic ring as the member of the ring

Z is O or S;

when X is N, Y is C=O or C=S, and the double line consisting of a solid line and a broken line is a single bond; and when X is C, Y is N, and the double line consisting of a solid line and a broken line is a double bond.

The invention further relates to an agent for preventing or treating zoster-associated pain in acute phase containing a diazepine derivative having the following formula (XIa) or a pharmacologically acceptable salt thereof as an active ingredient:

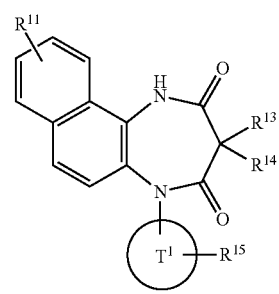

(XIa)

wherein $R^{11}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

each of $R^{13}$ and $R^{14}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{15}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

and the ring shown below is a heterocyclic ring selected from the group consisting of thiophene ring, pyridine ring, pyrimidine ring, quinoline ring, indole ring, indoline ring, benzimidazole ring, indazole ring, benzisoxazole ring, and benzotriazole ring, and the ring is combined with X at the carbon atom contained in the heterocyclic ring as the member of the ring;

The invention further relates to a compound having the following formula (XII) or a pharmacologically acceptable salt thereof:

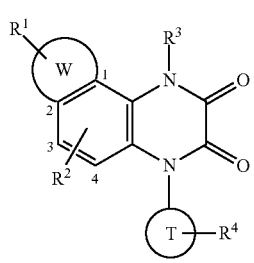

(XII)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or an aralkyl group comprising a $C_{6-10}$ aryl moiety and a $C_{1-3}$ alkylene moiety;

$R^4$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or more heteroatoms selected from N, S, and O as the members of the ring, and being condensed with the benzene ring at 1- and 2-positions of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, indazole ring, benzisoxazole ring, and benzotriazole ring.

The invention further relates to a compound having the following formula (XIIa) or a pharmacologically acceptable salt thereof:

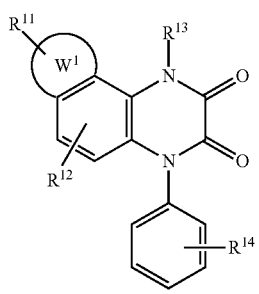

(XIIa)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a halogen atom, hydroxyl, nitro, cyano, amino, a C$_{1-8}$ alkylamino group, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, or sulfamoyl;

R$^{13}$ is hydrogen, a C$_{1-8}$ alkyl group, a C$_{2-8}$ alkenyl group, a C$_{1-8}$ alkyl group having one to three halogen atoms, or an aralkyl group comprising a C$_{6-10}$ aryl moiety and a C$_{1-3}$ alkylene moiety;

R$^{14}$ is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, an aralkyl group comprising a C$_{6-10}$ aryl moiety and a C$_{1-3}$ alkylene moiety, a C$_{1-8}$ alkyl group having hydroxyl, a halogen atom, hydroxyl, nitro, cyano, amino, a C$_{1-8}$ alkylamino group, a C$_{1-5}$ alkylamino group having one to five halogen atoms, a C$_{2-8}$ dialkylamino group, a C$_{2-8}$ acylamino group, a C$_{2-8}$ acylamino group having one to three halogen atoms, a C$_{1-8}$ alkylsulfonylamino group, benzenesulfonylamino optionally having one or more substituents, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

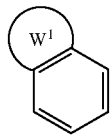

The invention further relates to a compound having the following formula (XIII) or a pharmacologically acceptable salt thereof:

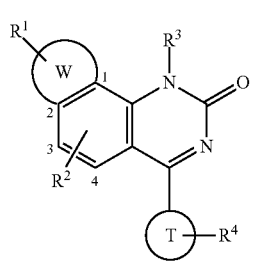

(XIII)

wherein each of R$^1$ and R$^2$ independently is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, an aralkyl group comprising a C$_{6-10}$ aryl moiety and a C$_{1-3}$ alkylene moiety, a halogen atom, hydroxyl, nitro, cyano, amino, a C$_{1-8}$ alkylamino group, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, or sulfamoyl;

R$^3$ is hydrogen, a C$_{1-8}$ alkyl group, a C$_{2-8}$ alkenyl group, a C$_{1-8}$ alkyl group having one to three halogen atoms, or an aralkyl group comprising a C$_{6-10}$ aryl moiety and a C$_{1-3}$ alkylene moiety;

R$^4$ is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, an aralkyl group comprising a C$_{6-10}$ aryl moiety and a C$_{1-3}$ alkylene moiety, a C$_{1-8}$ alkyl group having hydroxyl, a halogen atom, hydroxyl, nitro, cyano, amino, a C$_{1-8}$ alkylamino group, a C$_{1-5}$ alkylamino group having one to five halogen atoms, a C$_{2-8}$ dialkylamino group, a C$_{2-8}$ acylamino group, a C$_{2-8}$ acylamino group having one to three halogen atoms, a C$_{1-8}$ alkylsulfonylamino group, benzenesulfonylamino optionally having one or more substituents, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or two nitrogen atoms as the members of the ring, and being condensed with the benzene ring at 1- and 2-positions of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, pyrazole ring, indazole ring, benzisoxazole ring, and benzotriazole ring;

provided that R$^4$ is not hydrogen, a C$_{1-8}$ alkyl group, or a halogen atom in the case that the ring shown below is benzene ring.

The invention further relates to a compound having the following formula (XIIIa) or a pharmacologically acceptable salt thereof:

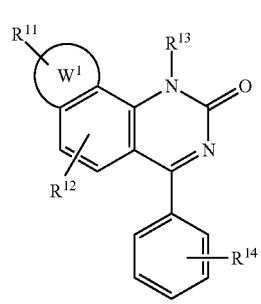

(XIIIa)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or an aralkyl group comprising a $C_{6-10}$ aryl moiety and a $C_{1-3}$ alkylene moiety;

$R^{14}$ is a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a $C_{1-8}$ alkyl group having hydroxyl, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

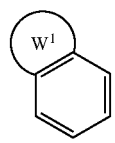

BRIEF DESCRIPTIONS OF THE DRAWINGS

FIG. 1 shows fluorescent double immunohistostaining images within the posterior horn area of spinal L5 after HSV-1 virus infection in Example 2.

The cells positive to both the OX42 antibody, which is expressed specific to the microglia, and the $P2X_4$ receptor antibody are brightly shown (the area indicated by the arrow and the area circled with the dotted line).

The right figures show HSV-1 virus inoculation, and the left figures show non-virus inoculation.

The upper figures show the whole image of the spinal posterior horn, and the lower figures show the enlarged image.

The right is a graph showing the influences of paroxetine seven days after virus inoculation, and the left is a graph showing the influences of paroxetine thirty 30 days after virus inoculation.

Figure 5:
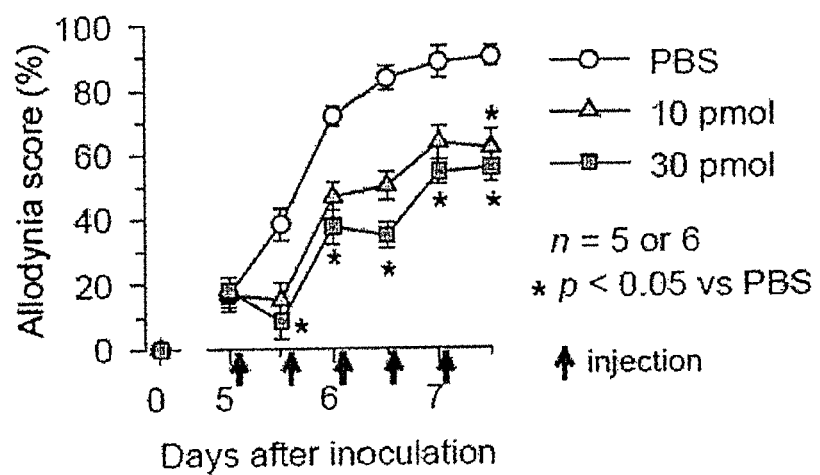

FIG. 5 is a graph showing the effect of the compound A on zoster-associated pain in acute phase in Example 4.

THE EMBODIMENTS OF THE INVENTION

The present invention is described below in more detail.

The active ingredients of the agent of the invention for preventing or treating zoster-associated pain in acute phase include the following compounds.
(1) $P2X_4$ receptor antagonist.
(2) A compound having the following formula (I) or a pharmacologically acceptable salt thereof:

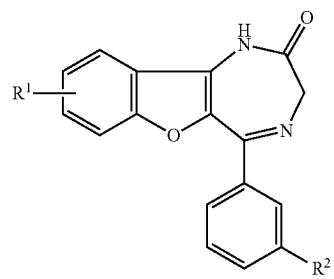

(I)

wherein $R^1$ is a halogen atom; and $R^2$ is hydrogen, a halogen atom, nitro, cyano, —C(O)—OR$^3$, —C(O)—NR$^4$R$^5$, —SO$_2$—OR$^3$, or —SO$_2$—NR$^4$R$^5$, wherein each of $R^3$, $R^4$, and $R^5$ is hydrogen or a $C_{1-6}$ alkyl group; or in the alternative $R^1$ is hydrogen; and $R^2$ is a halogen atom, nitro, cyano, —C(O)—OR$^3$, —C(O)—NR$^4$R$^5$, —SO$_2$—OR$^3$, or —SO$_2$—NR$^4$R$^5$, wherein each of $R^3$, $R^4$, and $R^5$ is hydrogen or a $C_{1-6}$ alkyl group.

(3) A compound having the formula (I) described in (2) or a pharmacologically acceptable salt thereof:

wherein $R^1$ is chloro or bromo; and $R^2$ is hydrogen, chloro, bromo, nitro, cyano, or —C(O)—OR$^3$, or —C(O)—NR$^4$R$^5$, wherein each of $R^3$, $R^4$, and $R^5$ is hydrogen or a $C_{1-4}$ alkyl group; or in the alternative $R^1$ is hydrogen; and $R^2$ is chloro, bromo, nitro, cyano, —C(O)—OR$^3$, or —C(O)—NR$^4$R$^5$, wherein each of $R^3$, $R^4$, and $R^5$ is hydrogen or a $C_{1-4}$ alkyl group.

(4) A compound having the following formula (Ia) or a pharmacologically acceptable salt thereof:

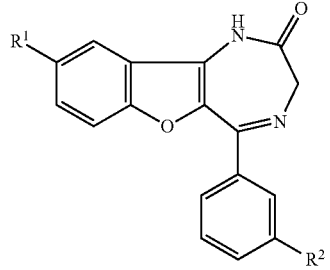

(Ia)

wherein $R^1$ is chloro or bromo; and $R^2$ is hydrogen, chloro, bromo, nitro, or cyano; or in the alternative $R^1$ is hydrogen; and $R^2$ is chloro, bromo, nitro, or cyano.

(5) A compound having the following formula (II) or a pharmacologically acceptable salt thereof:

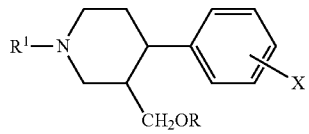

(II)

wherein R is a $C_{1-4}$ alkyl group, a $C_{2-4}$ alkynyl group, phenyl optionally having one or more substituents selected from the group consisting of a lower alkyl group, an alkylthio group, an alkoxy group, a halogen atom, nitro, an acylamino group, methylsulfonyl, and methylenedioxy, or tetrahydronaphthyl;
$R^1$ is hydrogen; and
X is hydrogen, a $C_{1-4}$ alkyl group, a trifluoroalkyl group, hydroxyl, a halogen atom, methylthio, or an arylalkoxy group.

(6) A selective serotonin reuptake inhibitor.

(7) Imipramine, nortriptyline, amitriptyline, desipramine, doxepin, fluoxetine, fluvoxamine, citalopram, or a pharmacologically acceptable salt thereof.

(8) A compound having the following formula (III) or a pharmacologically acceptable salt thereof:

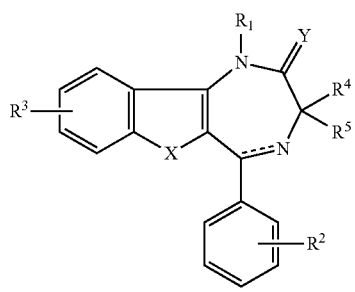

(III)

wherein X is S or $CH_2$;
Y is O, S, or NH;
$R^1$ is hydrogen, a $C_{1-8}$ alkyl group, a $C_{1-8}$ alkyl group having one or more halogen atoms, an aralkyl group comprising a $C_{1-6}$ alkyl moiety and a $C_{6-10}$ aryl moiety, a $C_{2-8}$ alkenyl group, carboxymethyl, or an alkoxycarbonylmethyl group comprising a $C_{1-8}$ alkoxy moiety;
each of $R^2$ and $R^3$ independently is hydrogen, a $C_{1-8}$ alkyl group, a $C_{1-8}$ alkoxy group, a $C_{1-8}$ alkyl group having one or more halogen atoms, a $C_{1-8}$ alkoxy group having one or more halogen atoms, a halogen atom, amino, carboxyl, hydroxyl, nitro, cyano, a $C_{2-8}$ acyl group, a $C_{6-10}$ aryl group, or a five-membered or six-membered heterocyclic group;
each of $R^4$ and $R^5$ independently is hydrogen, a $C_{1-8}$ alkyl group, or a $C_{1-8}$ alkyl group having one or more halogen atoms; and
the double line consisting of a broken line and a solid line is a single bond or a double bond.

(9) A compound having the formula (III) described in (8) or a pharmacologically acceptable salt thereof, wherein X is S.

(10) A compound having the formula (III) described in (8) or a pharmacologically acceptable salt thereof, wherein Y is O.

(11) A compound having the formula (III) described in (8) or a pharmacologically acceptable salt thereof, wherein $R^1$ is hydrogen or a $C_{1-8}$ alkyl group.

(12) A compound having the formula (III) described in (8) or a pharmacologically acceptable salt thereof, wherein each of $R^2$ and $R^3$ independently is hydrogen, a $C_{1-8}$ alkyl group, a $C_{1-8}$ alkoxy group, a $C_{1-8}$ alkyl group having one or more halogen atoms, a $C_{1-8}$ alkoxy group having one or more halogen atoms, a halogen atom, amino, carboxyl, hydroxyl, nitro, or cyano.

(13) A compound having the formula (III) described in (8) or a pharmacologically acceptable salt thereof, wherein $R^3$ is hydrogen, and $R^2$ is a halogen atom or hydroxyl.

(14) A compound having the formula (III) described in (8) or a pharmacologically acceptable salt thereof, wherein $R^2$ substitutes at meta-position.

(15) A compound having the formula (III) described in (8) or a pharmacologically acceptable salt thereof, wherein each of $R^4$ and $R^5$ is hydrogen.

(16) A compound having the formula (III) described in (8) or a pharmacologically acceptable salt thereof, wherein the double line consisting of a broken line and a solid line is a double bond.

(17) A compound having the following formula (IV) or a pharmacologically acceptable salt thereof:

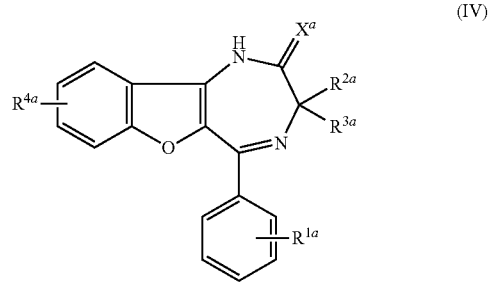

(IV)

wherein $X^a$ is O, S, or NH;
$R^{1a}$ is hydroxyl, tetrazolyl, $N(R^{5a})(R^{6a})$, a $C_{2-8}$ alkenyl group, a $C_{2-8}$ alkynyl group, a $C_{1-8}$ alkyl group having one or more halogen atoms, a $C_{1-8}$ alkoxy group having one or more halogen atoms, or a $C_{6-10}$ aryl group, wherein $R^{5a}$ is hydrogen or a $C_{1-8}$ alkyl group, and $R^{6a}$ is hydrogen, a $C_{1-8}$ alkyl group, or a $C_{2-8}$ acyl group;
each of $R^{2a}$ and $R^{3a}$ independently is hydrogen, a $C_{1-8}$ alkyl group, or a $C_{1-8}$ alkyl group having one or more halogen atoms; and
$R^{4a}$ is hydrogen, a $C_{1-8}$ alkyl group, a $C_{1-8}$ alkoxy group, a $C_{1-8}$ alkyl group having one or more halogen atoms, a halogen atom, hydroxyl, nitro, amino, carboxyl, tetrazolyl, cyano, a $C_{6-10}$ aryl group, or a five-membered or six-membered heterocyclic group.

(18) A compound having the formula (IV) described in (17) or a pharmacologically acceptable salt thereof, wherein $X^a$ is O.

(19) A compound having the formula (IV) described in (17) or a pharmacologically acceptable salt thereof, wherein $R^{1a}$ is hydroxyl, amino, a $C_{1-8}$ alkylamino group, a $C_{2-12}$ dialkylamino group, a $C_{1-8}$ alkyl group having one or more halogen atoms, or phenyl.

(20) A compound having the formula (IV) described in (17) or a pharmacologically acceptable salt thereof, wherein $R^{1a}$ substitutes at meta-position.

(21) A compound having the formula (IV) described in (17) or a pharmacologically acceptable salt thereof, wherein each of $R^{2a}$ and $R^{3a}$ is hydrogen.

(22) A compound having the formula (IV) described in (17) or a pharmacologically acceptable salt thereof, wherein $R^{4a}$ is hydrogen.

(23) A compound having the following formula (IVa) or a pharmacologically acceptable salt thereof:

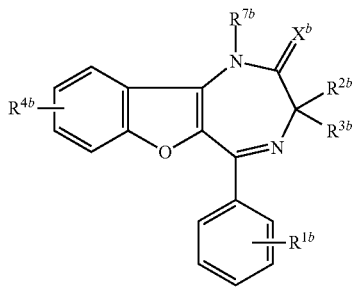

(IVa)

wherein $X^b$ is O, S, or NH;
$R^{1b}$ is a halogen atom, hydroxyl, tetrazolyl, $N(R^{5b})(R^{6b})$, a $C_{2-8}$ alkenyl group, a $C_{2-8}$ alkynyl group, a $C_{1-8}$ alkyl group having one or more halogen atoms, a $C_{1-8}$ alkoxy group having one or more halogen atoms, or a $C_{6-10}$ aryl group, wherein $R^{5b}$ is hydrogen or a $C_{1-8}$ alkyl group, and $R^{6b}$ is hydrogen, a $C_{1-8}$ alkyl group, or a $C_{2-8}$ acyl group;
each of $R^{2b}$ and $R^{3b}$ independently is hydrogen, a $C_{1-8}$ alkyl group, or a $C_{1-8}$ alkyl group having one or more halogen atoms;
$R^{4b}$ is hydrogen, a $C_{1-8}$ alkyl group, an alkoxy group, a $C_{1-8}$ alkyl group having one or more halogen atoms, a halogen atom, hydroxyl, nitro, amino, carboxyl, tetrazolyl, cyano, a $C_{6-10}$ aryl group, or a five-membered or six-membered heterocyclic group; and
$R^{7b}$ is a $C_{1-8}$ alkyl group.
(24) A compound having the formula (IVa) described in (23) or a pharmacologically acceptable salt thereof, wherein $X^b$ is O.
(25) A compound having the formula (IVa) described in (23) or a pharmacologically acceptable salt thereof, wherein $R^{1b}$ is a halogen atom, hydroxyl, amino, a $C_{1-8}$ alkylamino group, dialkylamino group, a $C_{1-8}$ alkyl group having one or more halogen atoms, or phenyl.
(26) A compound having the formula (IVa) described in (23) or a pharmacologically acceptable salt thereof, wherein $R^{1b}$ substitutes at meta-position.
(27) A compound having the formula (IVa) described in (23) or a pharmacologically acceptable salt thereof, wherein each of $R^{2b}$ and $R^{3b}$ is hydrogen.
(28) A compound having the formula (IVa) described in (23) or a pharmacologically acceptable salt thereof, wherein $R^{4b}$ is hydrogen.
(29) A compound having the following formula (IVb) or a pharmacologically acceptable salt thereof:

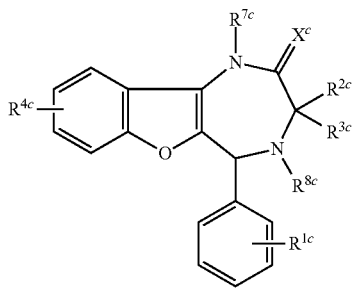

(IVb)

wherein $X^c$ is O, S, or NH;
$R^{1c}$ is hydrogen, a halogen atom, a $C_{1-8}$ alkyl group, a $C_{1-8}$ alkoxy group, hydroxyl, tetrazolyl, $N(R^{5c})(R^{6c})$, a $C_{2-8}$ alkenyl group, a $C_{2-8}$ alkynyl group, a $C_{1-8}$ alkyl group having one or more halogen atoms, a $C_{1-8}$ alkoxy group having one or more halogen atoms, or a $C_{6-10}$ aryl group, wherein $R^{5c}$ is hydrogen or a $C_{1-8}$ alkyl group, and $R^{6c}$ is hydrogen, a $C_{1-8}$ alkyl group, or a $C_{2-8}$ acyl group;
each of $R^{2c}$ and $R^{3c}$ independently is hydrogen, a $C_{1-8}$ alkyl group, or a $C_{1-8}$ alkyl group having one or more halogen atoms;
$R^{4c}$ is hydrogen, a $C_{1-8}$ alkyl group, an alkoxy group, a $C_{1-8}$ alkyl group having one or more halogen atoms, a halogen atom, hydroxyl, nitro, amino, carboxyl, tetrazolyl, cyano, a $C_{6-10}$ aryl group, or a five-membered or six-membered heterocyclic group;
$R^{7c}$ is hydrogen or a $C_{1-8}$ alkyl group; and
$R^{8c}$ is hydrogen, a $C_{1-8}$ alkyl group, or a $C_{2-8}$ acyl group.
(30) A compound having the formula (IVb) described in (29) or a pharmacologically acceptable salt thereof, wherein $X^c$ is O.
(31) A compound having the formula (IVb) described in (29) or a pharmacologically acceptable salt thereof, wherein $R^{1c}$ is hydrogen, a halogen atom, hydroxyl, amino, a $C_{1-8}$ alkylamino group, dialkylamino group, a $C_{1-8}$ alkyl group having one or more halogen atoms, or phenyl.
(32) A compound having the formula (IVb) described in (29) or a pharmacologically acceptable salt thereof, wherein $R^{1c}$ substitutes at meta-position.
(33) A compound having the formula (IVb) described in (29) or a pharmacologically acceptable salt thereof, wherein each of $R^{2c}$ and $R^{3c}$ is hydrogen.
(34) A compound having the formula (IVb) described in (29) or a pharmacologically acceptable salt thereof, wherein $R^{4c}$ is hydrogen or a halogen atom.
(35) A compound having the formula (IVb) described in (29) or a pharmacologically acceptable salt thereof, wherein $R^{7c}$ is hydrogen.
(36) A compound having the formula (IVb) described in (29) or a pharmacologically acceptable salt thereof, wherein $R^{8c}$ is hydrogen.
(37) A compound having the following formula (V) or a pharmacologically acceptable salt thereof:

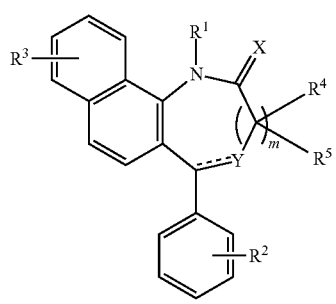

(V)

wherein X is O, S, or NH;
Y is N or $NR^6$, wherein $R^6$ is hydrogen or a $C_{1-8}$ alkyl group;
$R^1$ is hydrogen, a $C_{1-8}$ alkyl group, a $C_{2-8}$ alkenyl group, a $C_{1-8}$ alkyl group having one to three halogen atoms, or an alkyl group having phenyl;
$R^2$ is a $C_{1-8}$ alkyl group, a $C_{1-8}$ alkoxy group, a $C_{1-8}$ alkyl group having one to three halogen atoms, hydroxyl, nitro, amino, carboxyl, tetrazolyl, or cyano;

R³ is hydrogen, a C₁₋₈ alkyl group, a C₁₋₈ alkoxy group, a C₁₋₈ alkyl group having one to three halogen atoms, a halogen atom, hydroxyl, nitro, amino, carboxyl, tetrazolyl, or cyano;

each of R⁴ and R⁵ independently is hydrogen, a C₁₋₈ alkyl group, or a C₁₋₈ alkyl group having one to three halogen atoms;

m is 1 or 2;

when Y is N, the double line consisting of a solid line and a broken line is a double bond; and when Y is NR⁶, the double line consisting of a solid line and a broken line is a single bond.

(38) A compound having the formula (V) described in (37) or a pharmacologically acceptable salt thereof, wherein m is 1.

(39) A compound having the formula (V) described in (37) or a pharmacologically acceptable salt thereof, wherein X is O.

(40) A compound having the formula (V) described in (37) or a pharmacologically acceptable salt thereof, wherein Y is N.

(41) A compound having the formula (V) described in (37) or a pharmacologically acceptable salt thereof, wherein R¹ is hydrogen or a C₁₋₈ alkyl group.

(42) A compound having the formula (V) described in (37) or a pharmacologically acceptable salt thereof, wherein R¹ is hydrogen.

(43) A compound having the formula (V) described in (37) or a pharmacologically acceptable salt thereof, wherein each of R⁴ and R⁵ is hydrogen.

(44) A compound having the formula (V) described in (37) or a pharmacologically acceptable salt thereof, wherein R² is a C₁₋₈ alkyl group, a C₁₋₈ alkoxy group, a C₁₋₈ alkyl group having one to three halogen atoms, or hydroxyl.

(45) A compound having the formula (V) described in (37) or a pharmacologically acceptable salt thereof, wherein R² is a C₁₋₈ alkoxy group or hydroxyl.

(46) A compound having the formula (V) described in (37) or a pharmacologically acceptable salt thereof, wherein R³ is hydrogen or a halogen atom.

(47) A compound having the formula (V) described in (37) or a pharmacologically acceptable salt thereof, wherein R³ is hydrogen.

(48) A compound having the following formula (Va) or a pharmacologically acceptable salt thereof:

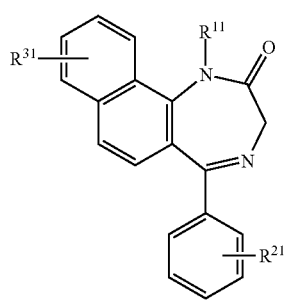

(Va)

wherein R¹¹ is hydrogen or a C₁₋₈ alkyl group;

R²¹ is a C₁₋₈ alkyl group, a C₁₋₈ alkoxy group, a C₁₋₈ alkyl group having one to three halogen atoms, or hydroxyl; and R³¹ is hydrogen or a halogen atom.

(49) A compound having the formula (Va) described in (48) or a pharmacologically acceptable salt thereof, wherein R¹¹ is hydrogen.

(50) A compound having the formula (Va) described in (48) or a pharmacologically acceptable salt thereof, wherein R²¹ is a C₁₋₈ alkoxy group or hydroxyl.

(51) A compound having the formula (Va) described in (48) or a pharmacologically acceptable salt thereof, wherein R³¹ is hydrogen.

(52) 5-(3-methoxyphenyl)-1,3-dihydro-2H-naphtho[1,2-e]-1,4-diazepin-2-one,
5-(3-hydroxyphenyl)-1,3-dihydro-2H-naphtho[1,2-e]-1,4-diazepin-2-one,
5-(4-methoxyphenyl)-1,3-dihydro-2H-naphtho[1,2-e]-1,4-diazepin-2-one,
5-(4-hydroxyphenyl)-1,3-dihydro-2H-naphtho[1,2-e]-1,4-diazepin-2-one,
5-(4-methylphenyl)-1,3-dihydro-2H-naphtho[1,2-e]-1,4-diazepin-2-one,
5-(2-methoxyphenyl)-1,3-dihydro-2H-naphtho[1,2-e]-1,4-diazepin-2-one,
5-(2-hydroxyphenyl)-1,3-dihydro-2H-naphtho[1,2-e]-1,4-diazepin-2-one,
5-(3,4-dimethoxyphenyl)-1,3-dihydro-2H-naphtho[1,2-e]-1,4-diazepin-2-one,
5-(3,4-dihydroxyphenyl)-1,3-dihydro-2H-naphtho[1,2-e]-1,4-diazepin-2-one, or
a pharmacologically acceptable salt thereof.

(53) A compound having the following formula (VI) or a pharmacologically acceptable salt thereof:

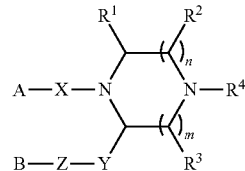

(VI)

wherein A is an aryl group optionally having one or more substituents or a heterocyclic group optionally having one or more substituents;

B is an aryl group optionally having one or more substituents or a heterocyclic group optionally having one or more substituents;

X is a C₁₋₅ alkylene group or a bond;

Y is a C₁₋₅ alkylene optionally comprising a double bond;

Z is O, S, N(R⁵), or a bond, wherein R⁵ is hydrogen or a C₁₋₈ alkyl group;

each of R¹, R², and R³ independently is hydrogen, a C₁₋₈ alkyl group, or a C₁₋₈ alkyl group having one to three halogen atoms;

R⁴ is hydrogen, a C₁₋₈ alkyl group, a C₁₋₈ alkyl group having one to three halogen atoms, a three-membered to seven-membered cycloalkyl group, or a C₁₋₈ alkyl group having a three-membered to seven-membered cycloalkyl group; and each of n and m independently is 1 or 2;

provided that when X is a bond, the substituent of the aryl group represented by A is not an alkyl group.

(54) A compound having the formula (VI) described in (53) or a pharmacologically acceptable salt thereof, wherein A is phenyl or thienyl, each of which optionally has one to three substituents selected from the group consisting of a halogen atom, a C₁₋₈ alkyl group (except that X is a bond), a C₁₋₈ alkyl group having one to three halogen atoms, nitro, cyano, hydroxyl, amino, a C₁₋₈ alkylamino group, a C₂₋₁₆ dialkylamino group, a C₂₋₈ acylamino group, a C₁₋₈ alkoxy group, a C$_{1-8}$ alkoxy group having one to three halogen atoms, an aryl group, and a heterocyclic group.

(55) A compound having the formula (VI) described in (53) or a pharmacologically acceptable salt thereof, wherein A is phenyl optionally having one to three substituents selected from the group consisting of selected from the group consisting of a halogen atom, a C$_{1-8}$ alkyl group (except that X is a bond), a C$_{1-8}$ alkoxy group, and a C$_{1-8}$ alkyl group having one to three halogen atoms.

(56) A compound having the formula (VI) described in (53) or a pharmacologically acceptable salt thereof, wherein B is phenyl, naphthyl, benzofuranyl, 1,3-benzo[d]dioxolyl, quinolyl, indolyl, benzothienyl, thienyl, or pyridyl, each of which optionally has one to three substituents selected from the group consisting of a halogen atom, a C$_{1-8}$ alkyl group, a C$_{1-8}$ alkyl group having one to three halogen atoms, nitro, cyano, hydroxyl, amino, a C$_{1-8}$ alkylamino group, a C$_{2-16}$ dialkylamino group, a C$_{2-8}$ acylamino group, a C$_{1-8}$ alkoxy group, a C$_{1-8}$ alkoxy group having one to three halogen atoms, a C$_{6-12}$ aryloxy group, a C$_{2-9}$ alkoxycarbonyl group, carbamoyl, a C$_{2-9}$ alkylcarbamoyl group, sulfamoyl, a C$_{1-8}$ alkylsulfamoyl group, and a C$_{2-16}$ dialkylsulfamoyl group.

(57) A compound having the formula (VI) described in (53) or a pharmacologically acceptable salt thereof, wherein B is phenyl, naphthyl, benzofuranyl, or 1,3-benzo[d]dioxolyl, each of which optionally has one to three substituents selected from the group consisting of a halogen atom, a C$_{1-8}$ alkyl group, a C$_{1-8}$ alkyl group having one to three halogen atoms, a C$_{1-8}$ alkoxy group, a C$_{6-12}$ aryloxy group, sulfamoyl, a C$_{1-8}$ alkylsulfamoyl group, and a C$_{2-16}$ dialkylsulfamoyl group.

(58) A compound having the formula (VI) described in (53) or a pharmacologically acceptable salt thereof, wherein X is a bond.

(59) A compound having the formula (VI) described in (53) or a pharmacologically acceptable salt thereof, wherein Y is methylene.

(60) A compound having the formula (VI) described in (53) or a pharmacologically acceptable salt thereof, wherein Z is O or S.

(61) A compound having the formula (VI) described in (53) or a pharmacologically acceptable salt thereof, wherein each of R$^1$, R$^2$, and R$^3$ is hydrogen.

(62) A compound having the formula (VI) described in (53) or a pharmacologically acceptable salt thereof, wherein R$^4$ is hydrogen or a C$_{1-8}$ alkyl group.

(63) A compound having the formula (VI) described in (53) or a pharmacologically acceptable salt thereof, wherein R$^4$ is hydrogen.

(64) A compound having the formula (VI) described in (53) or a pharmacologically acceptable salt thereof, wherein each of n and m is 1.

(65) A compound having the following formula (VIa) or a pharmacologically acceptable salt thereof:

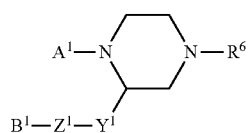

(VIa)

wherein A$^1$ is phenyl or thienyl, each of which optionally has one to three substituents selected from the group consisting of a halogen atom, a C$_{1-8}$ alkyl group having one to three halogen atoms, nitro, cyano, hydroxyl, amino, a C$_{1-8}$ alkylamino group, a C$_{2-16}$ dialkylamino group, a C$_{2-8}$ acylamino group, a C$_{1-8}$ alkoxy group, a C$_{1-8}$ alkoxy group having one to three halogen atoms, an aryl group, and a heterocyclic group;

B$^1$ is an aryl group optionally having one or more substituents or a heterocyclic group optionally having one or more substituents;

Y$^1$ is a C$_{1-5}$ alkylene chain optionally comprising a double bond;

Z$^1$ is O, S, N(R$^7$), or a bond, wherein R$^7$ is hydrogen or a C$_{1-8}$ alkyl group; and R$^6$ is hydrogen, a C$_{1-8}$ alkyl group, a C$_{1-8}$ alkyl group having one to three halogen atoms, or a three-membered to seven-membered cycloalkyl group.

(66) A compound having the formula (VIa) described in (65) or a pharmacologically acceptable salt thereof, wherein A$^1$ is phenyl optionally having one to three substituents selected from the group consisting of a halogen atom, a C$_{1-8}$ alkyl group having one to three halogen atoms, and a C$_{1-8}$ alkoxy group.

(67) A compound having the formula (VIa) described in (65) or a pharmacologically acceptable salt thereof, wherein B$^1$ is phenyl, naphthyl, benzofuranyl, 1,3-benzo[d]dioxolyl, quinolyl, indolyl, benzothienyl, thienyl, or pyridyl, each of which optionally has one to three substituents selected from the group consisting of a halogen atom, a C$_{1-8}$ alkyl group, a C$_{1-8}$ alkyl group having one to three halogen atoms, nitro, cyano, hydroxyl, amino, a C$_{1-8}$ alkylamino group, a C$_{2-16}$ dialkylamino group, a C$_{2-8}$ acylamino group, a C$_{1-8}$ alkoxy group, a C$_{1-8}$ alkoxy group having one to three halogen atoms, a C$_{6-12}$ aryloxy group, a C$_{2-9}$ alkoxycarbonyl group, carbamoyl, a C$_{2-9}$ alkylcarbamoyl group, sulfamoyl, a C$_{1-8}$ alkylsulfamoyl group and a C$_{2-16}$ dialkylsulfamoyl group.

(68) A compound having the formula (VIa) described in (65) or a pharmacologically acceptable salt thereof, wherein B$^1$ is phenyl, naphthyl, benzofuranyl, or 1,3-benzo[d]dioxolyl.

(69) A compound having the formula (VIa) described in (65) or a pharmacologically acceptable salt thereof, wherein Y$^1$ is methylene.

(70) A compound having the formula (VIa) described in (65) or a pharmacologically acceptable salt thereof, wherein Z$^1$ is O or S.

(71) A compound having the formula (VIa) described in (65) or a pharmacologically acceptable salt thereof, wherein R$^6$ is hydrogen or a C$_{1-8}$ alkyl group.

(72) A compound having the formula (VIa) described in (65) or a pharmacologically acceptable salt thereof, wherein R$^6$ is hydrogen.

(73) A compound having the following formula (VIb) or a pharmacologically acceptable salt thereof:

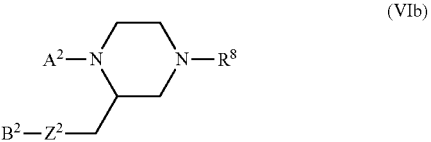

(VIb)

wherein A$^2$ is phenyl or thienyl, each of which optionally has one to three substituents selected from the group consisting of a halogen atom, a C$_{1-8}$ alkyl group having one to three halogen atoms, nitro, cyano, acetylamino, a C$_{1-8}$ alkoxy group, a C$_{1-8}$ alkoxy group having one to three halogen atoms, an aryl group, and a heterocyclic group;

B$^2$ is phenyl, naphthyl, benzofuranyl, 1,3-benzo[d]dioxolyl, quinolyl, indolyl, benzothienyl, thienyl, or pyridyl, each of which optionally has one to three substituents selected from the group consisting of a halogen atom, a $C_{1-8}$ alkyl group, a $C_{1-8}$ alkyl group having one to three halogen atoms, nitro, cyano, hydroxyl, amino, a $C_{2-8}$ acylamino group, a $C_{1-8}$ alkoxy group, a $C_{1-8}$ alkoxy group having one to three halogen atoms, a $C_{6-12}$ aryloxy group, sulfamoyl, a $C_{1-8}$ alkylsulfamoyl group, and a $C_{2-16}$ dialkylsulfamoyl group;

$Z^2$ is O, S, or NH; and $R^8$ is hydrogen or a $C_{1-8}$ alkyl group.

(74) A compound having the formula (VIb) described in (73) or a pharmacologically acceptable salt thereof, wherein $A^2$ is phenyl optionally having one to three substituents selected from the group consisting of a halogen atom, a $C_{1-8}$ alkyl group having one to three halogen atoms, a $C_{1-8}$ alkoxy group, nitro, cyano, or acetylamino.

(75) A compound having the formula (VIb) described in (73) or a pharmacologically acceptable salt thereof, wherein $A^2$ is phenyl optionally having one to three substituents selected from the group consisting of a halogen atom, a $C_{1-8}$ alkyl group having one to three halogen atoms, and a $C_{1-8}$ alkoxy group.

(76) A compound having the formula (VIb) described in (73) or a pharmacologically acceptable salt thereof, wherein $B^2$ is phenyl, naphthyl, benzofuranyl, or 1,3-benzo[d]dioxolyl, each of which optionally has one to three substituents selected from the group consisting of a halogen atom, a $C_{1-8}$ alkyl group, or a $C_{1-8}$ alkyl group having one to three halogen atoms, an aryloxy group, sulfamoyl, a $C_{1-8}$ alkylsulfamoyl group, and a $C_{2-16}$ dialkylsulfamoyl group.

(77) A compound having the formula (VIb) described in (73) or a pharmacologically acceptable salt thereof, wherein $Z^2$ is O or S.

(78) A compound having the formula (VIb) described in (73) or a pharmacologically acceptable salt thereof, wherein $R^8$ is hydrogen.

(79) 1-(4-fluorophenyl)-2-(4-phenoxyphenoxymethyl)piperazine, 1-(4-fluorophenyl)-2-(4-phenoxyphenylsulfanylmethyl)piperazine, 2-(4-chlorophenoxymethyl)-1-(4-isopropoxyphenyl)piperazine, 2-(2,4-dichlorophenoxymethyl)-1-(4-isopropoxyphenyl) piperazine, 2-(4-tert-butoxyphenoxymethyl)-1-(4-isopropoxyphenyl) piperazine, 2-(4-chlorophenoxymethyl)-1-(3-methoxyphenyl)piperazine, 2-(4-chlorophenoxymethyl)-1-(2-methoxyphenyl)piperazine, or a pharmacologically acceptable salt thereof.

(80) A compound having the following formula (VII) or a pharmacologically acceptable salt thereof:

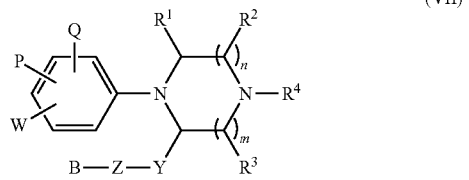

(VII)

wherein B is an aryl group optionally having one or more substituents or a heterocyclic group optionally having one or more substituents;

Y is a $C_{1-5}$ alkylene optionally comprising a double bond;

Z is O, S, N($R^5$), or a bond, wherein $R^5$ is hydrogen or a $C_{1-8}$ alkyl group;

each of R, $R^2$, and $R^3$ independently is hydrogen, a $C_{1-8}$ alkyl group, or a $C_{1-8}$ alkyl group having one to three halogen atoms;

$R^4$ is hydrogen, a $C_{1-8}$ alkyl group, a $C_{1-8}$ alkyl group having one to three halogen atoms, a three-membered to seven-membered cycloalkyl group, or a $C_{1-8}$ alkyl group having a three-membered to seven-membered cycloalkyl group;

each of P and Q independently is hydrogen, a halogen atom, a $C_{1-8}$ alkyl group, a $C_{1-8}$ alkyl group having one to three halogen atoms, nitro, cyano, hydroxyl, amino, a $C_{1-8}$ alkylamino group, a $C_{2-16}$ dialkylamino group, a $C_{2-8}$ acylamino group, a $C_{1-8}$ alkoxy group, a $C_{1-8}$ alkoxy group having one to three halogen atoms, or a heterocyclic group;

W is a $C_{1-8}$ alkyl group or a three-membered to seven-membered cycloalkyl group; or when P and W are placed at 2- and 3-positions or 3- and 4-positions of phenyl, P and W are combined to form propylene or tetramethylene; and each of n and m independently is 1 or 2.

(81) A compound having the formula (VII) described in (80) or a pharmacologically acceptable salt thereof, wherein B is phenyl, naphthyl, benzofuranyl, indolyl, benzothienyl, or thienyl optionally having one to three substituents selected from the group consisting of a halogen atom, a $C_{1-8}$ alkyl group, a $C_{1-8}$ alkyl group having one to three halogen atoms, nitro, cyano, hydroxyl, amino, a $C_{1-8}$ alkylamino group, a $C_{2-16}$ dialkylamino group, a $C_{2-8}$ acylamino group, a $C_{1-8}$ alkoxy group, a $C_{1-8}$ alkoxy group having one to three halogen atoms, a $C_{6-12}$ aryloxy group, an arylalkoxy group comprising a $C_{1-8}$ alkyl moiety, a $C_{2-9}$ alkoxycarbonyl group, carbamoyl, a $C_{2-9}$ alkylcarbamoyl group, sulfamoyl, a $C_{1-8}$ alkylsulfamoyl group, and a $C_{2-16}$ dialkylsulfamoyl group.

(82) A compound having the formula (VII) described in (80) or a pharmacologically acceptable salt thereof, wherein B is phenyl optionally having one to three substituents selected from the group consisting of selected from the group consisting of a halogen atom, a $C_{1-8}$ alkyl group, a $C_{1-8}$ alkyl group having one to three halogen atoms, nitro, cyano, hydroxyl, amino, a $C_{1-8}$ alkylamino group, a $C_{2-16}$ dialkylamino group, a $C_{2-8}$ acylamino group, a $C_{1-8}$ alkoxy group, a $C_{1-8}$ alkoxy group having one to three halogen atoms, a $C_{6-12}$ aryloxy group, an arylalkoxy group comprising a $C_{1-8}$ alkyl moiety, a $C_{2-9}$ alkoxycarbonyl group, carbamoyl, a $C_{2-9}$ alkylcarbamoyl group, sulfamoyl, a $C_{1-8}$ alkylsulfamoyl group, and a $C_{2-16}$ dialkylsulfamoyl group.

(83) A compound having the formula (VII) described in (80) or a pharmacologically acceptable salt thereof, wherein each of P and Q independently is hydrogen, a $C_{1-8}$ alkyl group, a $C_{1-8}$ alkyl group having one to three halogen atoms, or a $C_{1-8}$ alkoxy group.

(84) A compound having the formula (VII) described in (80) or a pharmacologically acceptable salt thereof, wherein each of P and Q is hydrogen.

(85) A compound having the formula (VII) described in (80) or a pharmacologically acceptable salt thereof, wherein W is a $C_{3-6}$ alkyl group.

(86) A compound having the formula (VII) described in (80) or a pharmacologically acceptable salt thereof, wherein W is n-propyl, isopropyl, n-butyl, or isobutyl.

(87) A compound having the formula (VII) described in (80) or a pharmacologically acceptable salt thereof, wherein each of n and m is 1.

(88) A compound having the formula (VII) described in (80) or a pharmacologically acceptable salt thereof, wherein Y is methylene.

(89) A compound having the formula (VII) described in (80) or a pharmacologically acceptable salt thereof, wherein Z is O or S.

(90) A compound having the formula (VII) described in (80) or a pharmacologically acceptable salt thereof, wherein each of $R^1$, $R^2$, and $R^3$ is hydrogen.

(91) A compound having the formula (VII) described in (80) or a pharmacologically acceptable salt thereof, wherein $R^4$ is hydrogen or a $C_{1-8}$ alkyl group.

(92) A compound having the formula (VII) described in (80) or a pharmacologically acceptable salt thereof, wherein $R^4$ is hydrogen.

(93) A compound having the formula (VII) described in (80) or a pharmacologically acceptable salt thereof: wherein $R^4$ is hydrogen;
Y is methylene;
Z is O or S; and
B is phenyl optionally having one to three substituents selected from the group consisting of a halogen atom, a $C_{1-8}$ alkyl group, a $C_{1-8}$ alkyl group having one to three halogen atoms, cyano, hydroxyl, a C-s alkoxy group, a $C_{1-8}$ alkoxy group having one to three halogen atoms, benzyloxy, sulfamoyl, and a $C_{1-8}$ alkylsulfamoyl group.

(94) 2-(4-chlorophenoxymethyl)-1-(4-isopropylphenyl)piperazine, 2-(4-chlorophenoxymethyl)-1-(4-propylphenyl) piperazine,
2-(4-chlorophenoxymethyl)-1-(3-isopropylphenyl)piperazine,
2-(4-chlorophenoxymethyl)-1-(2,4,6-trimethylphenyl)piperazine,
2-(4-chlorophenoxymethyl)-1-indan-5-yl-piperazine,
1-(4-isopropylphenyl)-2-[4-(isopropylsulfamoyl)phenoxymethyl]piperazine,
2-(4-chlorophenylsulfanylmethyl)-1-(4-isopropylphenyl) piperazine,
1-(3-isopropylphenyl)-2-[4-(isopropylsulfamoyl)phenoxymethyl]piperazine,
1-(4-isopropylphenyl)-2-(4-phenoxyphenoxymethyl)piperazine, or
a pharmacologically acceptable salt thereof.

(95) A compound having the following formula (VIII) or a pharmacologically acceptable salt thereof:

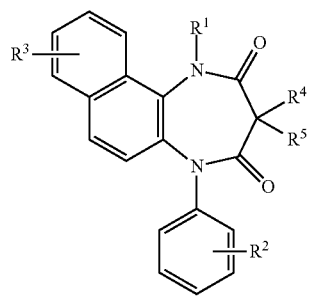

(VIII)

wherein $R^1$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

$R^2$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, carboxyl, a $C_{2-8}$ acyl group, or an alkoxycarbonyl group comprising a $C_{1-8}$ alkoxy moiety; and each of $R^4$ and $R^5$ independently is hydrogen, a $C_{1-8}$ alkyl group, or a $C_{1-8}$ alkyl group having one to three halogen atoms.

(96) A compound having the formula (VIII) described in (95) or a pharmacologically acceptable salt thereof, wherein $R^1$ is hydrogen or a $C_{1-8}$ alkyl group.

(97) A compound having the formula (VIII) described in (95) or a pharmacologically acceptable salt thereof, wherein $R^1$ is hydrogen.

(98) A compound having the formula (VIII) described in (95) or a pharmacologically acceptable salt thereof, wherein $R^4$ is hydrogen, and $R^5$ is hydrogen or a $C_{1-8}$ alkyl group.

(99) A compound having the formula (VIII) described in (95) or a pharmacologically acceptable salt thereof, wherein each of $R^4$ and $R^5$ is hydrogen.

(100) A compound having the formula (VIII) described in (95) or a pharmacologically acceptable salt thereof, wherein $R^2$ is a $C_{1-8}$ alkoxy group, hydroxyl, carboxyl, cyano, or an alkoxycarbonyl group comprising a $C_{1-8}$ alkoxy moiety.

(101) A compound having the formula (VIII) described in (95) or a pharmacologically acceptable salt thereof, wherein $R^2$ is a $C_{1-8}$ alkoxy group or hydroxyl.

(102) A compound having the formula (VIII) described in (95) or a pharmacologically acceptable salt thereof, wherein $R^3$ is hydrogen.

(103) A compound having the following formula (IX) or a pharmacologically acceptable salt thereof:

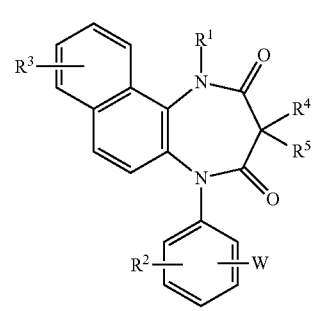

(IX)

wherein $R^1$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^2$ and $R^3$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

each of $R^4$ and $R^5$ independently is hydrogen, a $C_{1-8}$ alkyl group, a $C_{1-8}$ alkyl group having one to three halogen atoms, or a $C_{1-3}$ alkyl group having phenyl; and W is a five-membered or six-membered heterocyclic ring optionally having one or more substituents and comprising one to four nitrogen atoms as the members of the ring.

(104) A compound having the formula (IX) described in (103) or a pharmacologically acceptable salt thereof, wherein W is tetrazole, 1,2,4-triazole, 1,2,3-triazole, 1,2,4-oxadiazole, pyrazole, or imidazole, each of which optionally has one or more substituents selected from the group consisting of a $C_{1-8}$ alkyl group, a $C_{1-8}$ alkyl group having one to three halogen atoms, a halogen atom, cyano, oxo, and thioxo.

(105) A compound having the formula (IX) described in (103) or a pharmacologically acceptable salt thereof, wherein W is tetrazole, 1,2,4-triazole, or 1,2,3-triazole, each of which optionally has one or more substituents selected from the group consisting of a $C_{1-8}$ alkyl group, a $C_{1-8}$ alkyl group having one to three halogen atoms, a halogen atom, and cyano.

(106) A compound having the formula (IX) described in (103) or a pharmacologically acceptable salt thereof, wherein W is 5-oxo-1,2,4-oxadiazole or 5-thioxo-1,2,4-oxadiazole.

(107) A compound having the formula (IX) described in (103) or a pharmacologically acceptable salt thereof, wherein W is tetrazole.

(108) A compound having the formula (IX) described in (103) or a pharmacologically acceptable salt thereof, wherein $R^1$ is hydrogen or a $C_{1-8}$ alkyl group.

(109) A compound having the formula (IX) described in (103) or a pharmacologically acceptable salt thereof, wherein $R^1$ is hydrogen.

(110) A compound having the formula (IX) described in (103) or a pharmacologically acceptable salt thereof, wherein $R^4$ is hydrogen, and $R^5$ is hydrogen or a $C_{1-8}$ alkyl group.

(111) A compound having the formula (IX) described in (103) or a pharmacologically acceptable salt thereof, wherein each of $R^4$ and $R^5$ is hydrogen.

(112) A compound having the formula (IX) described in (103) or a pharmacologically acceptable salt thereof, wherein $R^2$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, carboxyl, a $C_{2-8}$ acyl group, or an alkoxycarbonyl group comprising a $C_{1-8}$ alkoxy moiety.

(113) A compound having the formula (IX) described in (103) or a pharmacologically acceptable salt thereof, wherein $R^2$ is hydrogen.

(114) A compound having the formula (IX) described in (103) or a pharmacologically acceptable salt thereof, wherein $R^3$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, carboxyl, a $C_{2-8}$ acyl group, or an alkoxycarbonyl group comprising a $C_{1-8}$ alkoxy moiety.

(115) A compound having the formula (IX) described in (103) or a pharmacologically acceptable salt thereof, wherein $R^3$ is hydrogen.

(116) 5-[3-(5-thioxo-4H-[1,2,4]oxadiazol-3-yl)phenyl]-1H-naphtho[1,2-b][1,4]diazepine-2,4(3H,5H)-dione sodium salt.

(117) Paroxetine or a pharmacologically acceptable salt thereof.

(118) A diazepine derivative having the following formula (X) or a pharmacologically acceptable salt thereof:

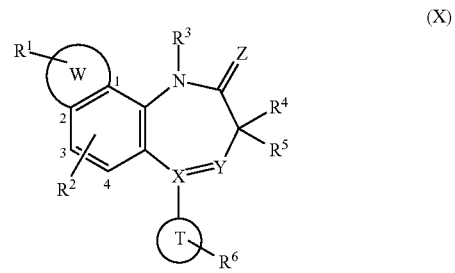

(X)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^4$ and $R^5$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^6$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered non-aromatic ring optionally comprising one or two heteroatoms selected from N, S, and O, and being condensed with the benzene ring at 1- and 2-positions of the benzene ring;

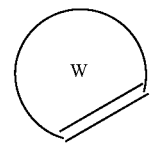

the ring shown below is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring;

Z is O or S;

when X is N, Y is C=O or C=S, and the double line consisting of a solid line and a broken line is a single bond; and when X is C, Y is N, and the double line consisting of a solid line and a broken line is a double bond.

(119) A diazepine derivative having the following formula (Xa) or a pharmacologically acceptable salt thereof:

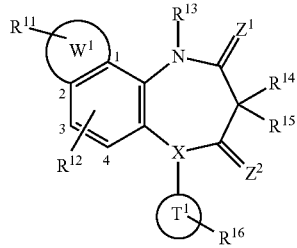

(Xa)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^{14}$ and $R^{15}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{16}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered non-aromatic ring optionally comprising one or two heteroatoms selected from N, S, and O, and being condensed with the benzene ring at 1- and 2-positions of the benzene ring;

the ring shown below is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring; and

each of $Z^1$ and $Z^2$ independently is O or S.

(120) A diazepine derivative having the formula (Xa) described in (119) or a pharmacologically acceptable salt thereof, wherein $R^{11}$ is hydrogen, a $C_{1-8}$ alkyl group, a $C_{2-8}$ alkenyl group, a $C_{1-8}$ alkyl group having one to three halogen atoms, a halogen atom, hydroxyl, amino, a $C_{1-8}$ alkylamino group, a $C_{2-8}$ dialkylamino group, or a $C_{2-8}$ acylamino group.

(121) A diazepine derivative having the formula (Xa) described in (119), (120), or a pharmacologically acceptable salt thereof, wherein $R^{12}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

(122) A diazepine derivative having the formula (Xa) described in one of (119) to (121) or a pharmacologically acceptable salt thereof, wherein $R^{13}$ is hydrogen, a $C_{1-8}$ alkyl group, or a $C_{1-8}$ alkyl group having one to three halogen atoms.

(123) A diazepine derivative having the formula (Xa) described in one of (119) to (122) or a pharmacologically acceptable salt thereof, wherein each of $R^{14}$ and $R^{15}$ independently is hydrogen, a $C_{1-8}$ alkyl group, or a $C_{1-8}$ alkyl group having one to three halogen atoms.

(124) A diazepine derivative having the formula (Xa) described in one of (119) to (123) or a pharmacologically acceptable salt thereof, wherein $R^{16}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituents.

(125) A diazepine derivative having the formula (Xa) described in one of (119) to (123) or a pharmacologically acceptable salt thereof, wherein $R^{16}$ is tetrazolyl, triazolyl, pyridyl, pyrazolyl, oxadiazolyl, isoxazolyl, pyrrolyl, pyrrolidinyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(126) A diazepine derivative having the formula (Xa) described in one of (119) to (123) or a pharmacologically acceptable salt thereof, wherein $R^{16}$ is tetrazolyl, triazolyl, pyridyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, and amino.

(127) A diazepine derivative having the formula (Xa) described in one of (119) to (126) or a pharmacologically acceptable salt thereof, wherein the ring shown below is tetrahydronaphthalene, indan, indoline, tetrahydroquinoline, or tetrahydroisoquinoline.

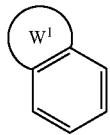

(128) A diazepine derivative having the formula (Xa) described in one of (119) to (127) or a pharmacologically acceptable salt thereof, wherein the ring shown below is benzene ring.

(129) A diazepine derivative having the formula (Xa) described in one of (119) to (128) or a pharmacologically acceptable salt thereof, wherein each of $Z^1$ and $Z^2$ is O.

(130) A diazepine derivative having the following formula (Xb) or a pharmacologically acceptable salt thereof:

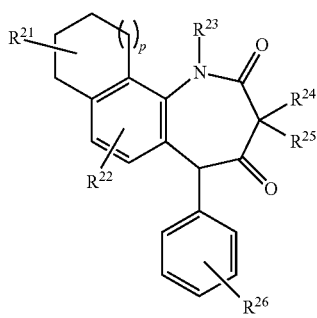

(Xb)

wherein each of $R^{21}$ and $R^{22}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{23}$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^{24}$ and $R^{25}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and p is 0 or 1.

(131) A diazepine derivative having the formula (Xb) described in (130) or a pharmacologically acceptable salt thereof, wherein $R^{21}$ is hydrogen, a $C_{1-8}$ alkyl group, a $C_{2-8}$ alkenyl group, a $C_{1-8}$ alkyl group having one to three halogen atoms, a halogen atom, hydroxyl, amino, a $C_{1-8}$ alkylamino group, a $C_{2-8}$ dialkylamino group, or a $C_{2-8}$ acylamino group.

(132) A diazepine derivative having the formula (Xb) described in (130), (131), or a pharmacologically acceptable salt thereof, wherein $R^{22}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

(133) A diazepine derivative having the formula (Xb) described in one of (130) to (132) or a pharmacologically acceptable salt thereof, wherein $R^{23}$ is hydrogen, a $C_{1-8}$ alkyl group, or a $C_{1-8}$ alkyl group having one to three halogen atoms.

(134) A diazepine derivative having the formula (Xb) described in one of (130) to (133) or a pharmacologically acceptable salt thereof, wherein each of $R^{24}$ and $R^{25}$ independently is hydrogen, a $C_{1-8}$ alkyl group, or a $C_{1-8}$ alkyl group having one to three halogen atoms.

(135) A diazepine derivative having the formula (Xb) described in one of (130) to (134) or a pharmacologically acceptable salt thereof, wherein $R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituents.

(136) A diazepine derivative having the formula (Xb) described in one of (130) to (134) or a pharmacologically acceptable salt thereof, wherein $R^{26}$ is tetrazolyl, triazolyl, pyridyl, pyrazolyl, oxadiazolyl, isoxazolyl, pyrrolyl, pyrrolidinyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(137) A diazepine derivative having the formula (Xb) described in one of (130) to (133) or a pharmacologically acceptable salt thereof, wherein $R^{26}$ is tetrazolyl, triazolyl, pyridyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, and amino.

(138) A diazepine derivative having the following formula (XI) or a pharmacologically acceptable salt thereof:

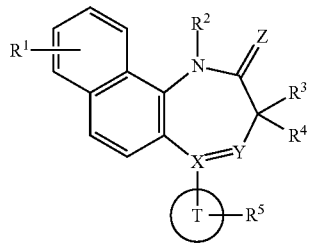

(XI)

wherein $R^1$ is hydrogen, a C-s alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^2$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^3$ and $R^4$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^5$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

X is C or N;

the ring shown below is a heterocyclic ring selected from the group consisting of thiophene ring, pyridine ring, pyrimidine ring, quinoline ring, indole ring, indoline ring, benzimidazole ring, indazole ring, benzisoxazole ring, and benzotriazole ring, and the ring is combined with X at the carbon atom contained in the heterocyclic ring as the member of the ring;

Z is O or S;

when X is N, Y is C=O or C=S, and the double line consisting of a solid line and a broken line is a single bond; and when X is C, Y is N, and the double line consisting of a solid line and a broken line is a double bond.

(139) A diazepine derivative having the formula (XI) described in (138) or a pharmacologically acceptable salt thereof, wherein $R^1$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

(140) A diazepine derivative having the formula (XI) described in (138), (139), or a pharmacologically acceptable salt thereof, wherein $R^2$ is hydrogen, a $C_{1-8}$ alkyl group, or a $C_{1-8}$ alkyl group having one to three halogen atoms.

(141) A diazepine derivative having the formula (XI) described in one of (138) to (140) or a pharmacologically acceptable salt thereof, wherein each of $R^3$ and $R^4$ independently is hydrogen, a $C_{1-8}$ alkyl group, or a $C_{1-8}$ alkyl group having one to three halogen atoms.

(142) A diazepine derivative having the formula (XI) described in one of (138) to (141) or a pharmacologically acceptable salt thereof, wherein $R^5$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituents.

(143) A diazepine derivative having the formula (XI) described in one of (138) to (141) or a pharmacologically acceptable salt thereof, wherein $R^5$ is tetrazolyl, triazolyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(144) A diazepine derivative having the formula (XI) described in one of (138) to (141) or a pharmacologically acceptable salt thereof, wherein $R^5$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, or hydroxyl.

(145) A diazepine derivative having the formula (XI) described in one of (138) to (144) or a pharmacologically acceptable salt thereof, wherein Z is O.

(146) A diazepine derivative having the following formula (XIa) or a pharmacologically acceptable salt thereof:

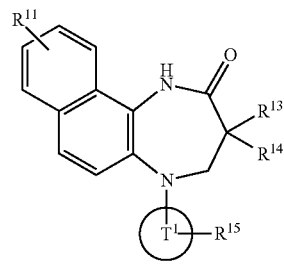

(XIa)

wherein $R^{11}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, or sulfamoyl;

each of R$^{13}$ and R$^{14}$ independently is hydrogen, a C$_{1-8}$ alkyl group, a C$_{1-8}$ alkyl group having one to three halogen atoms, a halogen atom, hydroxyl, nitro, cyano, amino, or a C$_{1-3}$ alkyl group having phenyl;

R$^{15}$ is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, a halogen atom, hydroxyl, nitro, cyano, amino, a C$_{1-8}$ alkylamino group, a C$_{1-5}$ alkylamino group having one to five halogen atoms, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, sulfamoyl, phenyl optionally having one or more substituents, or a heterocyclic group optionally having one or more substituents; and the ring shown below is a heterocyclic ring selected from the group consisting of thiophene ring, pyridine ring, pyrimidine ring, quinoline ring, indole ring, indoline ring, benzimidazole ring, indazole ring, benzisoxazole ring, and benzotriazole ring, and the ring is combined with X at the carbon atom contained in the heterocyclic ring as the member of the ring.

(147) A diazepine derivative having the formula (XIa) described in (146) or a pharmacologically acceptable salt thereof, wherein R$^{11}$ is hydrogen, a C$_{1-8}$ alkyl group, a C$_{1-8}$ alkoxy group, a C$_{1-8}$ alkyl group having one to three halogen atoms, a C$_{2-8}$ alkoxy group having one to three halogen atoms, a halogen atom, hydroxyl, nitro, cyano, amino, a C$_{1-8}$ alkylamino group, a C$_{2-8}$ dialkylamino group, a C$_{2-8}$ acylamino group, or a C$_{2-8}$ acylamino group having one to three halogen atoms.

(148) A diazepine derivative having the formula (XIa) described in (146) or a pharmacologically acceptable salt thereof, wherein R$^{11}$ is hydrogen, a C$_{1-8}$ alkyl group, a C$_{1-8}$ alkoxy group, a C$_{1-8}$ alkyl group having one to three halogen atoms, a C$_{1-8}$ alkoxy group having one to three halogen atoms, or a halogen atom.

(149) A diazepine derivative having the formula (XIa) described in one of (146) to (148) or a pharmacologically acceptable salt thereof, wherein each of R$^{13}$ and R$^{14}$ independently is hydrogen, a C$_{1-8}$ alkyl group, or a C$_{1-8}$ alkyl group having one to three halogen atoms.

(150) A diazepine derivative having the formula (XIa) described in one of (146) to (149) or a pharmacologically acceptable salt thereof, wherein R$^{15}$ is hydrogen, C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, a halogen atom, hydroxyl, nitro, cyano, amino, a C$_{1-8}$ alkylamino group, a C$_{2-8}$ dialkylamino group, or a heterocyclic group optionally having one or more substituents.

(151) A diazepine derivative having the formula (XIa) described in one of (146) to (149) or a pharmacologically acceptable salt thereof, wherein R$^{15}$ is tetrazolyl, triazolyl, imidazolyl, oxazolyl, or thiazolyl, each of which optionally has one or more substituents selected from the group consisting of a C$_{1-8}$ alkyl group, a C$_{1-8}$ alkoxy group, a C$_{1-8}$ alkyl group having one to three halogen atoms, a C$_{1-8}$ alkoxy group having one to three halogen atoms, a halogen atom, hydroxyl, nitro, cyano, amino, a C$_{1-8}$ alkylamino group, and a C$_{2-8}$ dialkylamino group.

(152) A diazepine derivative having the formula (XIa) described in one of (146) to (149) or a pharmacologically acceptable salt thereof, wherein R$^{15}$ is hydrogen, a C$_{1-8}$ alkyl group, a C$_{1-8}$ alkoxy group, a C$_{1-8}$ alkyl group having one to three halogen atoms, a C$_{1-8}$ alkoxy group having one to three halogen atoms or hydroxyl.

(153) A compound having the following formula (XII) or a pharmacologically acceptable salt thereof:

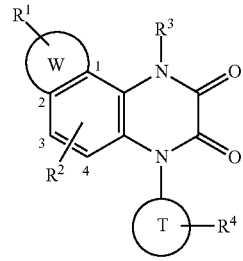

wherein each of R$^1$ and R$^2$ independently is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, an aralkyl group comprising a C$_{6-10}$ aryl moiety and a C$_{1-3}$ alkylene moiety, a halogen atom, hydroxyl, nitro, cyano, amino, a C$_{1-8}$ alkylamino group, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, or sulfamoyl;

R$^3$ is hydrogen, a C$_{1-8}$ alkyl group, a C$_{2-8}$ alkenyl group, a C$_{1-8}$ alkyl group having one to three halogen atoms, or an aralkyl group comprising a C$_{6-10}$ aryl moiety and a C$_{1-3}$ alkylene moiety;

R$^4$ is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, an aralkyl group comprising a C$_{6-10}$ aryl moiety and a C$_{1-3}$ alkylene moiety, a C$_{1-8}$ alkyl group having hydroxyl, a halogen atom, hydroxyl, nitro, cyano, amino, a C$_{1-8}$ alkylamino group, a C$_{1-5}$ alkylamino group having one to five halogen atoms, a C$_{2-8}$ dialkylamino group, a C$_{2-8}$ acylamino group, a C$_{2-8}$ acylamino group having one to three halogen atoms, a C$_{1-8}$ alkylsulfonylamino group, benzenesulfonylamino optionally having one or more substituents, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or more heteroatoms selected from N, S, and O as the members of the ring, and being condensed with the benzene ring at 1- and 2-positions of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, indazole ring, benzisoxazole ring, and benzotriazole ring.

(154) A compound having the formula (XII) described in (153) or a pharmacologically acceptable salt thereof, wherein each of $R^1$ and $R^2$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(155) A compound having the formula (XII) described in (153), (154), or a pharmacologically acceptable salt thereof, wherein $R^3$ is hydrogen or a $C_{1-8}$ alkyl group.

(156) A compound having the formula (XII) described in one of (153) to (155) or a pharmacologically acceptable salt thereof, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(157) A compound having the formula (XII) described in one of (153) to (155) or a pharmacologically acceptable salt thereof, wherein $R^4$ is tetrazolyl, triazolyl, pyridyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(158) A compound having the formula (XII) described in one of (153) to (155) or a pharmacologically acceptable salt thereof, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, amino, a $C_{1-8}$ alkylamino group, a $C_{2-8}$ dialkylamino group, or benzenesulfonylamino optionally having one or more substituents selected from the group consisting of a $C_{1-8}$ alkyl group, a $C_{1-8}$ alkoxy group, a halogen atom, and nitro.

(159) A compound having the formula (XII) described in one of (153) to (158) or a pharmacologically acceptable salt thereof, wherein the ring shown below is naphthalene ring, tetrahydronaphthalene ring, or indan ring.

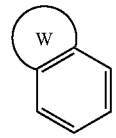

(160) A compound having the formula (XII) described in one of (153) to (159) or a pharmacologically acceptable salt thereof, wherein the ring shown below is benzene ring or indole ring.

(161) A compound having the following formula (XIIa) or a pharmacologically acceptable salt thereof:

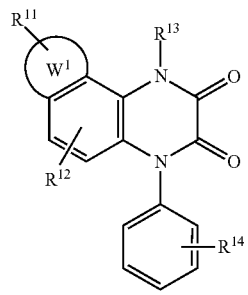

(XIIa)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or an aralkyl group comprising a $C_{6-10}$ aryl moiety and a $C_{1-3}$ alkylene moiety;

$R^{14}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

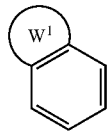

(162) A compound having the formula (XIIa) described in (161) or a pharmacologically acceptable salt thereof, wherein each of $R^{11}$ and $R^{12}$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(163) A compound having the formula (XIIa) described in (161), (162) or a pharmacologically acceptable salt thereof, wherein $R^{13}$ is hydrogen or a $C_{1-8}$ alkyl group.

(164) A compound having the formula (XIIa) described in one of (161) to (163) or a pharmacologically acceptable salt thereof, wherein $R^{14}$ is hydrogen, a $C_{1-8}$ alkyl group, a C-s alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(165) A compound having the formula (XIIa) described in one of (161) to (163) or a pharmacologically acceptable salt thereof, wherein $R^{14}$ is tetrazolyl, triazolyl, pyridyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(166) A compound having the formula (XIIa) described in one of (161) to (163) or a pharmacologically acceptable salt thereof, wherein $R^{14}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, amino, a $C_{1-8}$ alkylamino group, a $C_{2-8}$ dialkylamino group, or benzenesulfonylamino optionally having one or more substituents selected from the group consisting of a $C_{1-8}$ alkyl group, a $C_{1-8}$ alkoxy group, a halogen atom, and nitro.

(167) A compound having the formula (XIIa) described in one of (161) to (166) or a pharmacologically acceptable salt thereof, wherein the ring shown below is naphthalene ring.

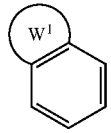

(168) A compound having the formula (XIIa) described in (161) or a pharmacologically acceptable salt thereof, wherein $R^{11}$, $R^{12}$, $R^{13}$, and the ring shown below are the same as those defined in (161), and $R^{14}$ is $NHSO_2R$, wherein R is an aryl group optionally having one or more substituents or a heterocyclic group optionally having one or more substituents.

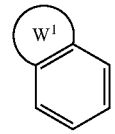

(169) A compound having the formula (XIIa) described in (168) or a pharmacologically acceptable salt thereof, wherein R is phenyl, naphthyl, quinolyl, pyridyl, or thienyl, which of which optionally has one or more substituents, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, hydroxyl, amino, nitro, or a halogen atom.

(170) A compound having the following formula (XIII) or a pharmacologically acceptable salt thereof:

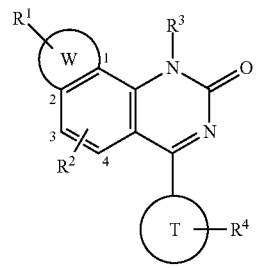

(XIII)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or an aralkyl group comprising a $C_{6-10}$ aryl moiety and a $C_{1-3}$ alkylene moiety;

$R^4$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or two nitrogen atoms as the members of the ring, and being condensed with the benzene ring at 1- and 2-positions of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, pyrazole ring, indazole ring, benzisoxazole ring, and benzotriazole ring;

provided that $R^4$ is not hydrogen, a $C_{1-8}$ alkyl group, or a halogen atom in the case that the ring shown below is benzene ring.

(171) A compound having the formula (XIII) described in (170) or a pharmacologically acceptable salt thereof, wherein each of $R^1$ and $R^2$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.
(172) A compound having the formula (XIII) described in (170), (171), or a pharmacologically acceptable salt thereof, wherein $R^3$ is hydrogen or a $C_{1-8}$ alkyl group.
(173) A compound having the formula (XIII) described in one of (170) to (172) or a pharmacologically acceptable salt thereof, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.
(174) A compound having the formula (XIII) described in one of (170) to (172) or a pharmacologically acceptable salt thereof, wherein $R^4$ is tetrazolyl, triazolyl, pyridyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.
(175) A compound having the formula (XIII) described in one of (170) to (172) or a pharmacologically acceptable salt thereof, wherein $R^4$ is a $C_{1-8}$ alkoxy group, a $C_{1-8}$ alkyl group having one to three halogen atoms, a $C_{1-8}$ alkoxy group having one to three halogen atoms, hydroxyl, cyano, amino, a $C_{1-8}$ alkylamino group, a $C_{2-8}$ dialkylamino group, or benzenesulfonylamino optionally having one or more substituents selected from the group consisting of a $C_{1-8}$ alkyl group, a $C_{1-8}$ alkoxy group, a halogen atom, and nitro.
(176) A compound having the formula (XIII) described in one of (170) to (175) or a pharmacologically acceptable salt thereof, wherein the ring shown below is naphthalene ring, tetrahydronaphthalene ring, or indan ring.

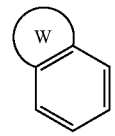

(177) A compound having the formula (XIII) described in one of (170) to (176) or a pharmacologically acceptable salt thereof, wherein the ring shown below is benzene ring or indole ring.

(178) A compound having the following formula (XIIIa) or a pharmacologically acceptable salt thereof:

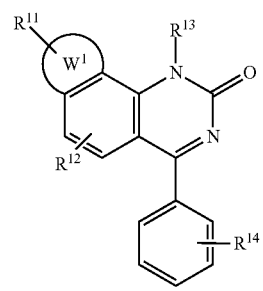

(XIIIa)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;
$R^{13}$ is hydrogen, a $C_{1-8}$ alkyl group, a $C_{2-8}$ alkenyl group, a $C_{1-8}$ alkyl group having one to three halogen atoms, or an aralkyl group comprising a $C_{6-10}$ aryl moiety and a $C_{1-3}$ alkylene moiety;
$R^{14}$ is a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group comprising a $C_{6-10}$ aryl moiety and a $C_{1-3}$ alkylene moiety, a $C_{1-8}$ alkyl group having hydroxyl, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

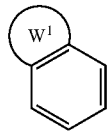

(179) A compound having the formula (XIIIa) described in (178) or a pharmacologically acceptable salt thereof, wherein each of $R^{11}$ and $R^{12}$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(180) A compound having the formula (XIIIa) described in (178), (179), or a pharmacologically acceptable salt thereof, wherein $R^{13}$ is hydrogen.

(181) A compound having the formula (XIIIa) described in one of (178) to (180) or a pharmacologically acceptable salt thereof, wherein $R^{14}$ is a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(182) A compound having the formula (XIIIa) described in one of (178) to (180) or a pharmacologically acceptable salt thereof, wherein $R^{14}$ is tetrazolyl, triazolyl, pyridyl, imidazolyl, oxazolyl, or thiazolyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(183) A compound having the formula (XIIIa) described in one of (178) to (180) or a pharmacologically acceptable salt thereof, wherein $R^{14}$ is a $C_{1-8}$ alkoxy group, a $C_{1-8}$ alkyl group having one to three halogen atoms, a $C_{1-8}$ alkoxy group having one to three halogen atoms, hydroxyl, cyano, amino, a $C_{1-8}$ alkylamino group, a $C_{2-8}$ dialkylamino group, or benzenesulfonylamino optionally having one or more substituents selected from the group consisting of a $C_{1-8}$ alkyl group, a $C_{1-8}$ alkoxy group, a halogen atom, and nitro.

(184) A compound having the formula (XIIIa) described in one of (178) to (183) or a pharmacologically acceptable salt thereof, wherein the ring shown below is naphthalene ring.

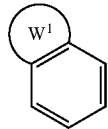

(185) 5-[3-(1H-tetrazole-5-yl)phenyl]-8,9,10,11-tetrahydronaphtho[2,1-b][1,4]diazepine-2,4(3H,5H)-dione sodium salt, 5-(1H-indol-6-yl)-1H-naphtho[1,2-b][1,4]diazepine-2,4(3H,5H)-dione, 4-[3-(1H-tetrazole-5-yl)phenyl]-1,4-dihydrobenzo[f]quinoxaline-2,3-dione sodium salt, or 4-[3-(1H-tetrazole-5-yl)phenyl]-1H-benzo[h]quinazolin-2-one sodium salt.

The above-mentioned compounds can be prepared according to known processes. For example, the compounds described in (2) to (4) can be prepared according to a process described in WO 2004/085440. The compounds described in (5) and (117) can be prepared according to a process described in Japanese Patent Publication No. 59(1984)-48826. The compounds described in (8) to (16) can be prepared according to a process described in WO 2007/072974. The compounds described in (17) to (36) can be prepared according to a process described in WO 2007/074970. The compounds described in (37) to (52) can be prepared according to a process described in WO 2008/023847. The compounds described in (53) to (79) can be prepared according to a process described in WO 2009/022730. The compounds described in (80) to (94) can be prepared according to a process described in WO 2009/022731. The compounds described in (95) to (102) can be prepared according to a process described in WO 2010/090300. The compounds described in (103) to (116) can be prepared according to a process described in WO 2010/093061.

The compounds described in (7) and (117) such as paroxetine, imipramine are known compounds. The chemical structures and the documents disclosing the processes for preparation of the compounds are described in The MERCK INDEX FOURTEENTH RDITION (2006) or the like. Further, these compounds are commercially available.

The selective serotonin reuptake inhibitors described in (6) include paroxetine, fluoxetine, fluvoxamine, and citalopram.

The above-mentioned WO 2004/085440, WO 2007/072974, WO 2007/074970, WO 2008/023847, WO 2009/022730, WO 2009/022731, WO 2010/090300, WO 2010/093061, WO 2007/049825, and WO 2008/020651 describe that the compounds described in (2) to (117) have $P2X_4$ receptor antagonism.

The compounds described in (118) to (185) also have P2X4 receptor antagonism, and can be prepared according to the processes described in the documents cited in the processes for preparation of the compounds described in (2) to (5) and (8) to (116).

The pharmacologically acceptable salts in the active ingredients of the present invention include a salt with an acid (e.g., as hydrochloric acid, acetic acid, benzoic acid, fumaric acid, besylic acid), an alkali metal (e.g., sodium, potassium, lithium), or an amine.

The active ingredients of the present invention can be a geometrical (cis-trans) isomer or an optical isomer such as an optically active substance and racemic modification, each of which is included within the scope of the invention. Hydrates can also be used as the active ingredients of the present invention.

The results of the pharmacological experiments are described below.

The effect of $P2X_4$ receptor antagonist on herpes zoster-associated pain in acute phase was examined using a mouse model (Examples 3 and 4).

Figure 4:
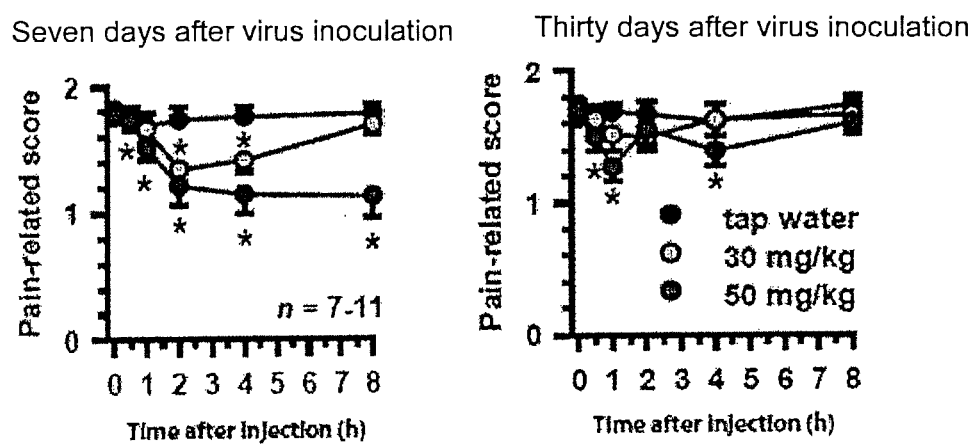
FIG. 4 is graphs showing influences of oral administration of paroxetine on acute phase pain of herpes zoster in Example 3.

The results of Examples 3 and 4 as well as FIGS. 4 and 5 show analgesic activities of paroxetine and the compound A (5-[3-(5-thioxo-4H-[1,2,4]oxadiazol-3-yl)phenyl]-1H-naphtho[1,2-b][1,4]diazepine-2,4(3H,5H)-dione sodium salt), which have $P2X_4$ receptor antagonism, on an acute phase of herpes zoster-induced pain. The results suggest that $P2X_4$ receptor plays a major role in the acute phase of herpes zoster-induced pain.

Further, immunohistological analysis and real time RT-PCR analysis using the mouse model of herpes zoster show that spinal microglial cells proliferate in the acute phase of herpes zoster, and that expression of $P2X_4$ receptor is increased in activated microglia. The results suggest that, in acute phase of the herpes zoster, spinal microglia become activated with proliferation and increase expression of $P2X_4$ receptors (Example 2, FIGS. 1-3) Accordingly, proliferation and activation of microglia and $P2X_4$ receptor with development of the syndrome of the herpes zoster in acute phase play important roles in causing the acute phase pain by herpes zoster. Therefore, it is suggested that $P2X_4$ receptor antagonist can be an effective therapeutic agent for acute phase pain of herpes zoster.

Aciclovir, Valaciclovir, and Famciclovir are conventional anti-herpetic drugs and have been used for treating herpes zoster in acute phase. It has been reported that they have an effect of accelerating healing exanthema and may shorten the duration of the zoster-associated pain (Wood M J, et al., Clin Infect Dis, 1996, 22:341-347; Beutner K R, et al., Antimicrob Agents Chemother, 1995, 39:1546-1553; Tyring S K., Semin Dermatol, 1996, 15:27-31; Wood M J, et al., N Engl J Med, 1994, 330:896-900; Rowbotham M C., Semin Nuerol, 1994, 14:247-254; Wood M J, et al., Am J Med, 1988, 85:79-83; Huff J C, et al., Am J Med, 1988, 85:84-89; and McKendrick M W, et al., BMJ, 1989, 298:431). It has also been suggested that continuous desensitization is necessary for preventing acute phase pain of herpes zoster from changing into postherpetic neuralgia (Manabe et al., Clin J Pain, 1995, 11:220-228). Therefore, it is suggested that combinations of the above-mentioned drugs with the $P2X_4$ receptor antagonist may show a stronger analgesic activity by removing acute phase pain to prevent or treat the postherpetic neuralgia.

The preventive or therapeutic agent of the present invention can be administered to human beings by ordinary administration methods such as oral administration or parenteral administration.

The compound can be granulated in ordinary manners for the preparation of pharmaceuticals. For instance, the compound can be processed to give tablets, granule, powder, capsule, suspension, injection, suppository, and the like.

Ordinary additives such as vehicles, disintegrators, binders, lubricants, dyes, and diluents are used for the preparation of these pharmaceuticals such as tablets. As the vehicles, lactose, D-mannitol, crystalline cellulose, and glucose can be mentioned. Further, there can be mentioned starch and carboxymethylcellulose calcium (CMC-Ca) as the disintegrators, magnesium stearate and talc as the lubricants, and hydroxylpropylcellulose (HPC), gelatin and polyvinylpyrrolidone (PVP) as the binders. The preparation of an injection can be made using solvents, stabilizers, dissolution-aids, suspensions, emulsifiers, soothing agents, buffers, or preservatives.

The compound of the invention can be administered to an adult generally in an amount of approximately 0.01 mg to 100 mg a day by parenteral administration and 1 mg to 2,000 mg a day by oral administration. The dosage can be adjusted in consideration of age and conditions of the patient.

EXAMPLES

Example 1

Experimental Procedure $P2X_4$ receptor antagonisms of the compound A (5-[3-(5-thioxo-4H-[1,2,4]oxadiazol-3-yl)phenyl]-1H-naphtho[1,2-b][1,4]diazepine-2,4(3H,5H)-dione sodium salt; described in Example 14 of WO 2010/093061) and paroxetine were measured as described below.

ATP receptors (human $P2X_4$) were introduced into 1321N1 cells, and used as a stable ATP receptorexpressing system. The obtained $P2X_4$ expressing 1321N1 cells were plated in a 96-well assay plate, and cultured 24 hours at 37° C. in an atmosphere of 5% $CO_2$ for calcium assay. Fura-2 AM calcium fluorescent indicator was dissolved in an extracellular solution for calcium imaging. The obtained solution was loaded onto the plated cells, and placed at room temperature for 45 minutes to introduce Fura-2 AM into the cells. The fluorescence was detected by FLUOstar OPTIMA micro plate reader (BMG Labtech). The cells were alternatively illuminated with two excitations wavelengths (340 nm and 380 nm) via xenon lamp, and the emitted fluorescence was measured at 510 nm. The fluorescence changes after the treatment of 1 μM ATP were monitored and determined the fluorescence ratio (F340/F380) as the index of intracellular calcium change. Tested compounds were treated to cells 15 min before the addition of ATP, and the inhibitory activities of compounds were calculated by comparing the Ca2+ response with control in the absence of tested compound.

Experimental Results

TABLE 1

| Test compound | $IC_{50}$ (μM) |
|---|---|
| Paroxetine | 4.6 |
| Compound A | 0.27 |

Example 2

Immunohistological and RT-real time PCR analyses were conducted using the mouse model of herpes zoster to study that spinal microglia cells proliferate in acute phase of herpes zoster, and expression of $P2X_4$ receptor increases in activated microglia.

Experimental Procedure

Epidermis of the right hind leg (lower part of knee joint) of shaven female C57BL/6J mice was chopped with a bundle of ten 26 G injection needles, and coated with a solution ($1\times10^6$ pfu/site) of herpes simplex virus Type I (HSV-1), which as well as varicella zoster virus, belongs to Herpesviridae (family) (Takasaki I, et al., Anesthesiology, 2002, 96:1168-1174). Seven days after infection, the spinal cord was collected after perfusion of 4% neutral buffered paraformaldehyde, replaced with 30% sucrose solution, embedded with OCT compound to prepare frozen slices. A specimen in cross section was prepared at the fifth lumbar level of the spinal cord, and was subjected to a fluorescent double immunostaining according to Alexa Fluor 488, 546 using OX42 antibody, which has widely been used as a microglia marker, and $P2X_4$ receptor antibody.

Experimental Results

Figure 1:
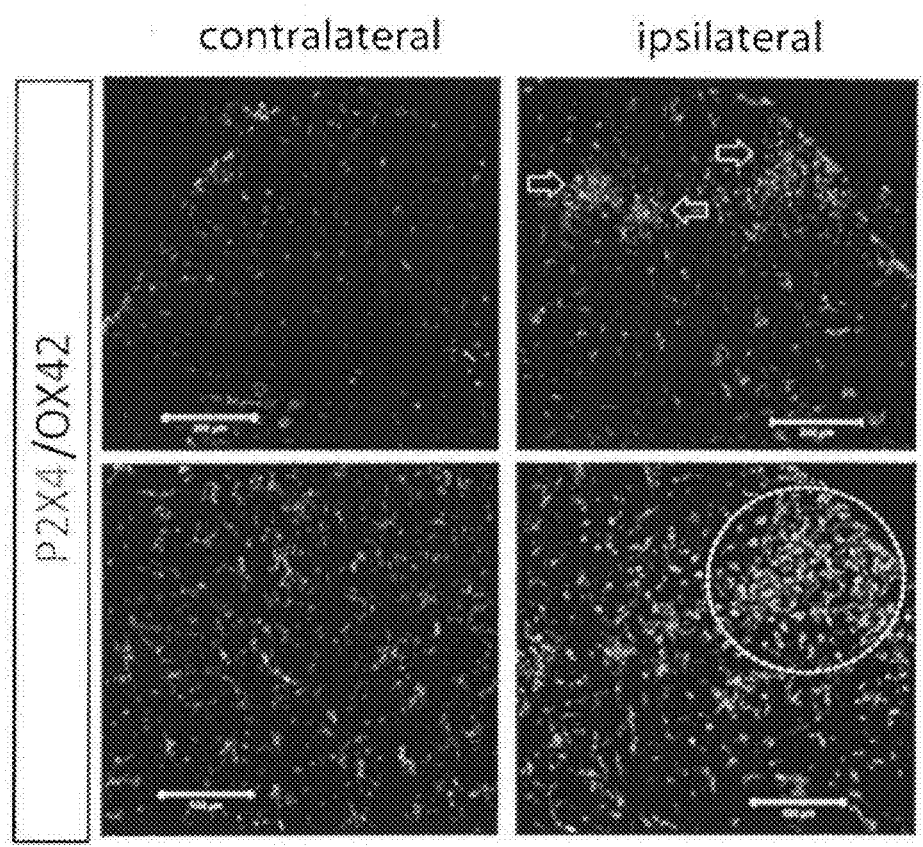

The obtained fluorescent immunostaining images are shown in FIG. 1. Seven days after infection, immunofluorescence intensities of OX42 (microglia marker) and $P2X_4$ receptor increase on the side treated with HSV-1 (right figures) within L5 segment of the spinal cord, compared with the side with no HSV-1 treatment (left figures). Further, it is observed that the two signals are co-localized clearly (the area indicated by the arrow in the upper right figure and the area circled with the dotted line in the lower right figure).

Figure 2:
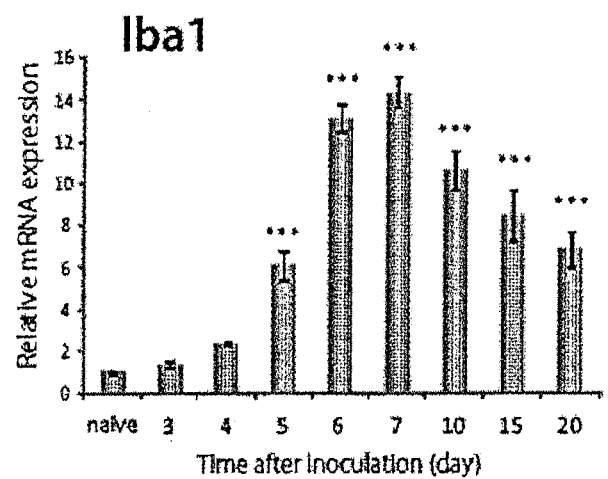
FIG. 2 is a graph showing the results of the RT-real time PCR analysis using Iba1 protein mRNA expression changes caused by herpes zoster manifestation in Example 2.
Figure 3:
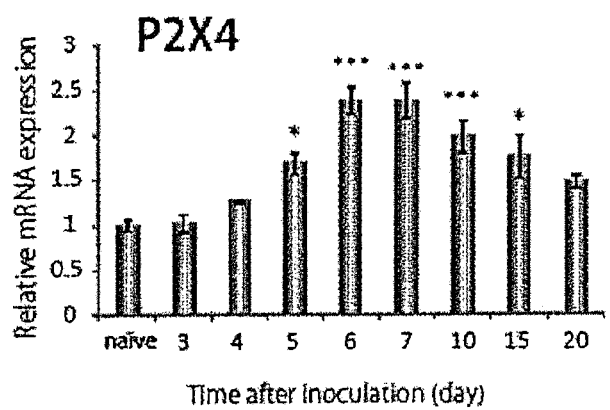
FIG. 3 is a graph showing the results of RT-real time PCR analysis of mRNA expression of $P2X_4$ receptor protein caused by herpes zoster manifestation in Example 2.

The results of RT-real time PCR analysis of the herpes zoster manifestation are shown in FIG. 2. Mice were infected with HSV-1 to cause manifestation of herpes zoster. The total RNA was extracted from the L5 segment of the spinal cord from third day to twentieth day in the acute phase, and subjected to a reverse transcription to obtain cDNA. The changes in mRNA expression of Iba1, which is a calcium-binding protein with microglia-specific expression, and $P2X_4$ receptor was studied using a Taq Man real time PCR method. The Iba1 mRNA expression was significantly increased from five days to twenty days after infection, and the increase peaked at day seven (FIG. 2). With respect to $P2X_4$ receptor, a peak was also observed seven days after infection, and significant increase was observed from five days to fifteen days after infection (FIG. 3). As is evident from the results, the time-course of the increase in mRNA expressions of Iba1 (microglia marker) and $P2X_4$ receptor was almost same. Taken these results together, it is suggested that the expression of $P2X_4$ receptors in the spinal cord is increased in the proliferated microglia that occurs in the acute phase of herpes zoster.

Example 3

Experimental Procedure

The effect of $P2X_4$ receptor antagonist in zoster-associated pain in acute phase was studied using the mouse model of herpes zoster described in Example 2. At seven days after infection corresponding to the time of zoster-associated pain in acute phase and thirty days after infection corresponding to the time of postherpetic neuralgia, paroxetine (30 mg/kg, 50 mg/kg) or the solvent (tap water) was orally administered. It has been reported that paroxetine functions as an inhibitor of $P2X_4$ receptor (Nagata K, Imai T et al., Molecular Pain, 2009, 5:20). The pain-associated reaction of the hindpaw on the HSV-1 infection side was measured and evaluated referring to the response to a contact stimulant using a paint-brush. The mouse was placed into a cage for measurement, and accustomed to the environment for 1 hour or more. The plantar surface of the right hindpaw was vertically stroked with the paintbrush along the direction from toe to heal, and this was repeated six times at intervals of several seconds. The pain reaction was evaluated as follows:
Score 0: No reaction
Score 1: Lifting of hind leg
Score 2: Sharp evasion reaction and flinching of hind leg
Each individual pain score was calculated by averaging six scores.

Experimental Results

FIG. 4 shows influence of oral administration of paroxetine on acute phase pain of herpes zoster. Mice were inoculated with HSV-1, and the pain score reached the almost maximum seven days after infection. Seven days after infection, threshold of the pain was significantly improved from 1 hour to 4 hours after administration of paroxetine (30 mg/kg) into the mice. In the group of administration of 50 mg/kg of paroxetine, it was observed that threshold of the pain was continuously improved from 30 minutes to 8 hours after administration (the right figure of FIG. 4). Thirty days after infection, 30 mg/kg of paroxetine did not show any significant improvement on the threshold of the pain, and only in the group of 50 mg/kg of paroxetine, significant improvement was observed on the threshold of the pain 30 minutes, 1 hour, and 4 hours after administration (the left figure of FIG. 4).

Example 4

Experimental Procedure

The effect of $P2X_4$ receptor antagonism on zoster-associated pain in acute phase was studied using the mouse model of herpes zoster described in Example 2. From five days to seven days after infection corresponding to the time of zoster-associated pain in acute phase, the compound A (10 pmol/mouse, 30 pmol/mouse), which is a $P2X_4$ receptor-specific antagonist, or PBS was intrathecally administered twice a day, at AM 10:00 to 11:00 and PM 6:00 to 7:00. Threshold of the pain was measured before administration of the drug (AM 9:30 to 10:00 and PM 5:30 to 6:00). Pain-associated reaction on the HSV-1 infection side hindpaw was measured using von Frey Filament (0.16 g). The mouse was placed into a cage for measurement, and accustomed to the environment for 1 hour or more. The von Frey filament was vertically applied to the right hindpaw for three to five seconds to bend the filament slightly, and this was repeated six times at intervals of several seconds. The pain reaction was evaluated as follows:
Score 0: No reaction
Score 1: Lifting of hind leg
Score 2: Sharp evasion reaction and flinching of hind leg
Each individual pain score was calculated by averaging six scores. The allodynia score (%) was calculated as the average score of each group by counting the maximum reaction score 2 as 100%.

Experimental Results

FIG. 5 shows the influence of intrathecal administration of the compound A on acute phase pain of herpes zoster.

The arrow in the graph indicates the time of the intrathecal administration of the compound A (10 pmol/mouse, 30 pmol/mouse) or PBS twice a day at AM 10:00 to 11:00 and at PM 6:00 to 7:00 after five days to seven days after infection. Threshold of the pain was measured before administration of the drugs (AM 9:30 to 10:00 and PM 5:30 to 6:00).

In the group of mice inoculated with HSV-1 and administered with PBS, the pain score reached the almost maximum seven days after infection. In the groups administered with 10 pmol/mouse and 30 pmol/mouse of the compound A, it was observed that the threshold score of the pain was significantly suppressed compared with the pain threshold score after the first administration.

What is claimed is:
1. A method of treating prodrome or pain of herpes zoster in acute phase comprising administrating an effective amount of a compound having the following formula (VIII) or a pharmacologically acceptable salt thereof to a patient in need thereof:

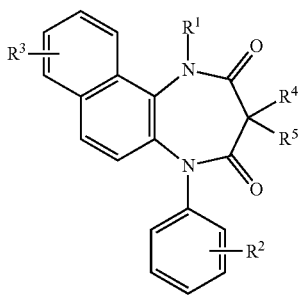

(VIII)

wherein $R^1$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

$R^2$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, carboxyl, a $C_{2-8}$ acyl group, or an alkoxycarbonyl group comprising a $C_{1-8}$ alkoxy moiety; and each of $R^4$ and $R^5$ independently is hydrogen, a $C_{1-8}$ alkyl group, or a $C_{1-8}$ alkyl group having one to three halogen atoms.

2. The method according to claim 1, wherein $R^1$ is hydrogen.

3. The method according to claim 1, wherein each of $R^4$ and $R^5$ is hydrogen.

4. The method according to claim 1, wherein $R^2$ is a $C_{2-8}$ acylamino group having one to three halogen atoms.

5. The method according to claim 1, wherein $R^3$ is hydrogen.

* * * * *